US011199333B2

(12) United States Patent
Rosen et al.

(10) Patent No.: US 11,199,333 B2
(45) Date of Patent: Dec. 14, 2021

(54) INTELLIGENT PURIFIER LIGHT

(71) Applicant: Resilience Magnum IP, LLC, Cleveland, OH (US)

(72) Inventors: Steven Rosen, Hunting Valley, OH (US); Ronald Cozean, Madison, CT (US); Eric Allen, Long Beach, CA (US); David Edward Mordetzky, Oak Park, CA (US); Megan Horvath, Cleveland, OH (US); Anthony John Pyros, Cleveland, OH (US); John Elwood, Santa Ana, CA (US); Michael Chang, Long Beach, CA (US); Elie Attarian, Chatsworth, CA (US)

(73) Assignee: RESILIENCE MAGNUM IP, LLC, Cleveland, OH (US)

( * ) Notice: Subject to any disclaimer, the term of this patent is extended or adjusted under 35 U.S.C. 154(b) by 0 days.

(21) Appl. No.: 17/005,534

(22) Filed: Aug. 28, 2020

(65) Prior Publication Data

US 2020/0393146 A1 Dec. 17, 2020

Related U.S. Application Data

(63) Continuation of application No. 16/043,949, filed on Jul. 24, 2018, now Pat. No. 10,794,603.

(Continued)

(51) Int. Cl.
*A61L 2/00* (2006.01)
*A61L 2/08* (2006.01)
(Continued)

(52) U.S. Cl.
CPC ............... *F24F 8/10* (2021.01); *A61L 2/08* (2013.01); *B01D 46/0086* (2013.01);
(Continued)

(58) Field of Classification Search
CPC ....... F24F 3/1603; A61L 2/08; B01D 46/0086
See application file for complete search history.

(56) References Cited

U.S. PATENT DOCUMENTS

| 6,147,624 A | 11/2000 | Clapper |
| 6,236,303 B1 | 5/2001 | Wagner et al. |

(Continued)

FOREIGN PATENT DOCUMENTS

| CN | 105371177 A | 3/2016 |
| CN | 105959380 A | 9/2016 |

OTHER PUBLICATIONS

Final Office Action received for U.S. Appl. No. 16/044,027 dated Oct. 8, 2020, 29 pages.

(Continued)

Primary Examiner — Robert A Hopkins
(74) Attorney, Agent, or Firm — Amin, Turocy & Watson, LLP

(57) ABSTRACT

Techniques for purifier light are provided. A purifier light can determine characteristics of the environment in which the purifier light is installed, determine capabilities of purifier light, determine one or more objectives of the installation of purifier light related to purification of the environment, perform a self-configuration of purifier light according to the determined one or more objectives, and determine and execute suitable actions for purifier light to perform to achieve the determined one or more objectives.

20 Claims, 17 Drawing Sheets

Related U.S. Application Data

(60) Provisional application No. 62/625,484, filed on Feb. 2, 2018, provisional application No. 62/568,294, filed on Oct. 4, 2017.

(51) Int. Cl.
   *F24F 8/10* (2021.01)
   *G01N 21/94* (2006.01)
   *B01D 46/00* (2006.01)
   *F21V 33/00* (2006.01)
   *B01D 46/44* (2006.01)

(52) U.S. Cl.
   CPC ............ *B01D 46/442* (2013.01); *F21V 33/00* (2013.01); *G01N 21/94* (2013.01); *F24F 2221/02* (2013.01)

(56) References Cited

U.S. PATENT DOCUMENTS

| | | |
|---|---|---|
| 6,528,954 B1 | 3/2003 | Lys |
| 6,946,974 B1 | 9/2005 | Racunas, Jr. |
| 7,026,954 B2 | 4/2006 | Slemmer et al. |
| 7,111,952 B2 | 9/2006 | Veskovic |
| 7,824,065 B2 | 11/2010 | Maxik |
| 8,280,558 B2 | 10/2012 | Picco |
| 8,283,812 B2 | 10/2012 | Azancot et al. |
| 8,362,713 B2 | 1/2013 | Recker et al. |
| 8,545,033 B2 | 10/2013 | Gielen |
| 8,600,786 B2 | 12/2013 | Stefik et al. |
| 8,674,616 B2 | 3/2014 | Holman et al. |
| 8,950,461 B2 | 2/2015 | Adams et al. |
| 9,367,050 B2 | 6/2016 | Jain et al. |
| 9,560,388 B2 | 1/2017 | Ogle et al. |
| 9,594,956 B2 | 3/2017 | Cohen et al. |
| 9,595,193 B1 | 3/2017 | Duale et al. |
| 9,601,018 B2 | 3/2017 | Cogill et al. |
| 9,644,799 B2 | 5/2017 | Crayford et al. |
| 9,700,641 B2 * | 7/2017 | Hawkins ............... A61L 9/20 |
| 9,893,551 B2 | 2/2018 | Cheatham, III et al. |
| 9,938,765 B2 | 4/2018 | Berman et al. |
| 10,210,355 B1 | 2/2019 | Lai |
| 10,251,242 B1 | 4/2019 | Rosen et al. |
| 10,677,402 B2 | 6/2020 | Rosen et al. |
| 10,867,486 B2 | 12/2020 | Rosen et al. |
| 2002/0171562 A1 | 11/2002 | Muraki |
| 2004/0022058 A1 | 2/2004 | Birrell |
| 2005/0128751 A1 | 6/2005 | Roberge et al. |
| 2005/0248299 A1 | 11/2005 | Chemel et al. |
| 2006/0044798 A1 | 3/2006 | Pazula |
| 2006/0197684 A1 | 9/2006 | Tremblay |
| 2008/0191009 A1 | 8/2008 | Gressel et al. |
| 2009/0059603 A1 | 3/2009 | Recker et al. |
| 2009/0303079 A1 | 12/2009 | Khim |
| 2010/0007525 A1 | 1/2010 | Shanbhag et al. |
| 2010/0060485 A1 | 3/2010 | Kim |
| 2010/0309024 A1 | 12/2010 | Mimeault |
| 2011/0006893 A1 | 1/2011 | Finch et al. |
| 2011/0193872 A1 | 8/2011 | Biemath et al. |
| 2012/0011033 A1 | 1/2012 | Salgia |
| 2012/0066144 A1 | 3/2012 | Berkvens et al. |
| 2012/0092192 A1 | 4/2012 | Wong |
| 2012/0098655 A1 | 4/2012 | Preta et al. |
| 2013/0002587 A1 | 1/2013 | Biggs et al. |
| 2013/0073350 A1 | 3/2013 | Blustein |
| 2013/0113936 A1 | 5/2013 | Cohen et al. |
| 2013/0300911 A1 | 11/2013 | Beckman |
| 2014/0049963 A1 | 2/2014 | McGuire |
| 2014/0049972 A1 | 2/2014 | McGuire |
| 2014/0055990 A1 | 2/2014 | Reed |
| 2014/0217914 A1 | 8/2014 | Maxik |
| 2014/0262057 A1 | 9/2014 | Chambers et al. |
| 2015/0195100 A1 | 7/2015 | Imes et al. |
| 2015/0286938 A1 | 10/2015 | Blair et al. |
| 2016/0047164 A1 | 2/2016 | Lundy et al. |
| 2016/0085884 A1 | 3/2016 | Schafer et al. |
| 2016/0135271 A1 | 3/2016 | Alexander |
| 2016/0104325 A1 | 4/2016 | Lu |
| 2016/0216443 A1 | 7/2016 | Morgan et al. |
| 2016/0359325 A1 | 12/2016 | Kawata et al. |
| 2017/0073074 A1 | 3/2017 | Gagnon et al. |
| 2017/0094756 A1 | 3/2017 | Saffari |
| 2017/0192406 A1 | 7/2017 | Ashdown et al. |
| 2017/0247289 A1 | 8/2017 | Waldschmidt et al. |
| 2017/0322350 A1 | 11/2017 | Montagne |
| 2018/0096634 A1 | 4/2018 | Walker et al. |
| 2018/0154032 A1 | 6/2018 | Dombrovsky |
| 2018/0156429 A1 | 6/2018 | Carlet et al. |
| 2018/0163934 A1 | 6/2018 | Miller |
| 2018/0167516 A1 | 6/2018 | Warrick |
| 2018/0211503 A1 | 7/2018 | Baliga et al. |
| 2018/0216791 A1 | 8/2018 | Leung et al. |
| 2018/0224596 A1 | 8/2018 | Creasman et al. |
| 2018/0259141 A1 | 9/2018 | Yamaguchi et al. |
| 2018/0313660 A1 | 11/2018 | Eyster et al. |
| 2019/0069379 A1 | 2/2019 | Kastee et al. |
| 2019/0104181 A1 | 4/2019 | Rosen et al. |

OTHER PUBLICATIONS

Non-Final Office Action received for U.S. Appl. No. 16/856,434 dated Sep. 1, 2020, 50 pages.
Final Office Action received for U.S. Appl. No. 16/682,085 dated Oct. 28, 2020, 27 pages.
Final Office Action received for U.S. Appl. No. 16/682,085 dated Oct. 8, 2020, 29 pages.
Non-Final Office Action received for U.S. Appl. No. 16/739,627 dated Apr. 26, 2021, 31 pages.
Non-Final Office Action received for U.S. Appl. No. 16/043,875 dated May 26, 2021, 45 pages.
Non-Final Office Action received for U.S. Appl. No. 16/044,027 dated Jun. 9, 2021, 29 pages.
Non-Final Office Action received for U.S. Appl. No. 17/062,929 dated May 5, 2021, 38 pages.
Final Office Action received for U.S. Appl. No. 16/043,875 dated Jan. 25, 2020, 13 pages.
Non-Final Office Action received for U.S. Appl. No. 16/044,047 dated Dec. 26, 2018, 22 pages.
Notice of Allowance received for U.S. Appl. No. 16/044,073 dated Nov. 8, 2018, 20 pages.
Non-Final Office Action received for U.S. Appl. No. 16/043,974 dated May 2, 2019, 28 pages.
Non-Final Office Action received for U.S. Appl. No. 16/043,798 dated Jun. 27, 2019, 15 pages.
Non-Final Office Action received for U.S. Appl. No. 16/130,720 dated Jul. 25, 2019, 37 pages.
Non-Final Office Action received for U.S. Appl. No. 16/270,646 dated Aug. 21, 2019, 29 pages.
Non-Final Office Action received for U.S. Appl. No. 16/739,627 dated Febuary 7, 2020, 19 pages.
Non-Final Office Action received for U.S. Appl. No. 16/544,023 dated Apr. 9, 2020, 28 pages.
Non-Final Office Action received for U.S. Appl. No. 16/043,997 dated Apr. 8, 2020, 46 pages.
Non-Final Office Action received for U.S. Appl. No. 16/821,007 dated May 1, 2020, 36 pages.
Non-Final Office Action received for U.S. Appl. No. 16/044,027 dated Jun. 22, 2020, 48 pages.
Notice of Allowance received for U.S. Appl. No. 16/043,949 dated May 21, 2020, 49 pages.
Non-Final Office Action received for U.S. Appl. No. 16/043,875 dated May 27, 2020, 15 pages.
Non-Final Office Action received for U.S. Appl. No. 16/043,875 dated Jul. 8, 2020, 36 pages.
Notice of Allowance received for U.S. Appl. No. 16/043,997 dated Aug. 7, 2020, 46 pages.
Non-Final Office Action received for U.S. Appl. No. 17/099,928 dated Jun. 24, 2021, 53 pages.

(56) References Cited

OTHER PUBLICATIONS

Notice of Allowance received for U.S. Appl. No. 17/005,534 dated Aug. 4, 2021, 50 pages.
Notice of Allowance received for U.S. Appl. No. 17/062,929 dated Aug. 9, 2021, 27 pages.
Final Office Action received for U.S. Appl. No. 16/739,627 dated Sep. 30, 2021, 33 pages.
Non-Final Office Action received for U.S. Appl. No. 17/099,898 dated Sep. 24, 2021, 68 pages.

* cited by examiner

INTELLIGENT PURIFIER LIGHT

CROSS-REFERENCE TO RELATED APPLICATIONS

This application is a continuation of, and claims priority to each of, pending U.S. patent application Ser. No. 16/043,949, filed on Jul. 24, 2018, entitled "INTELLIGENT PURIFIER LIGHT", which claims priority to U.S. Provisional Patent Application Ser. No. 62/625,484 filed on Feb. 2, 2018, entitled "INTELLIGENT PURIFIER LIGHT" and U.S. Provisional Patent Application Ser. No. 62/568,294 filed on Oct. 4, 2017, entitled "SELF AWARE LIGHTS THAT SELF-CONFIGURE." The entireties of the aforementioned applications are incorporated by reference herein.

BACKGROUND

The subject disclosure relates generally to lights that purify surfaces and/or areas.

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, systems, computer-implemented methods, apparatus and/or computer program products that facilitate a purifier light performing actions to purify contaminants in an environment are described.

According to an embodiment, a purifier light bulb is provided. The purifier light bulb comprises one or more instruments, a memory that stores computer executable components, and a processor that executes the computer executable components stored in the memory. The computer executable components can comprise: an operation component that: employs at least one instrument of the one or more instruments to monitor a contamination level of a contaminant in an environment in which purifier light is installed; in response to a determination that the contamination level of the contaminant does not satisfy a defined cleanliness criterion, determines at least one action to perform to achieve at least one objective on the installation of the purifier light related to purification of the contaminant in the environment; and executes the at least one action.

In another embodiment, a purifier light is provided. The purifier light comprises a purifier light fixture, a purifier light bulb configured for installation in the purifier light fixture, one or more instruments located in at least one of the purifier light bulb or the purifier light fixture, a memory that stores computer executable components, and a processor that executes the computer executable components stored in the memory. The computer executable components can comprise: an operation component that: employs at least one instrument of the one or more instruments to monitor a contamination level of a contaminant in an environment in which purifier light is installed; in response to a determination that the contamination level of the contaminant does not satisfy a defined cleanliness criterion, determines at least one action to perform to achieve at least one objective on the installation of the purifier light related to purification of the contaminant in the environment; and executes the at least one action.

In another embodiment, a method comprises: determining, by a purifier light bulb via one or more instruments of the purifier light bulb, one or more characteristics of an environment in which purifier light bulb is installed; determining, by the purifier light bulb, one or more capabilities of the purifier light bulb; generating, by the purifier light bulb, one or more objectives for the purifier light bulb related to purification of the environment based on the one or more characteristics and the one or more capabilities; and configuring, by the purifier light bulb, at least one setting of at least one parameter of the purifier light bulb to achieve the one or more objectives.

DETAILED DESCRIPTION

Figure 1:
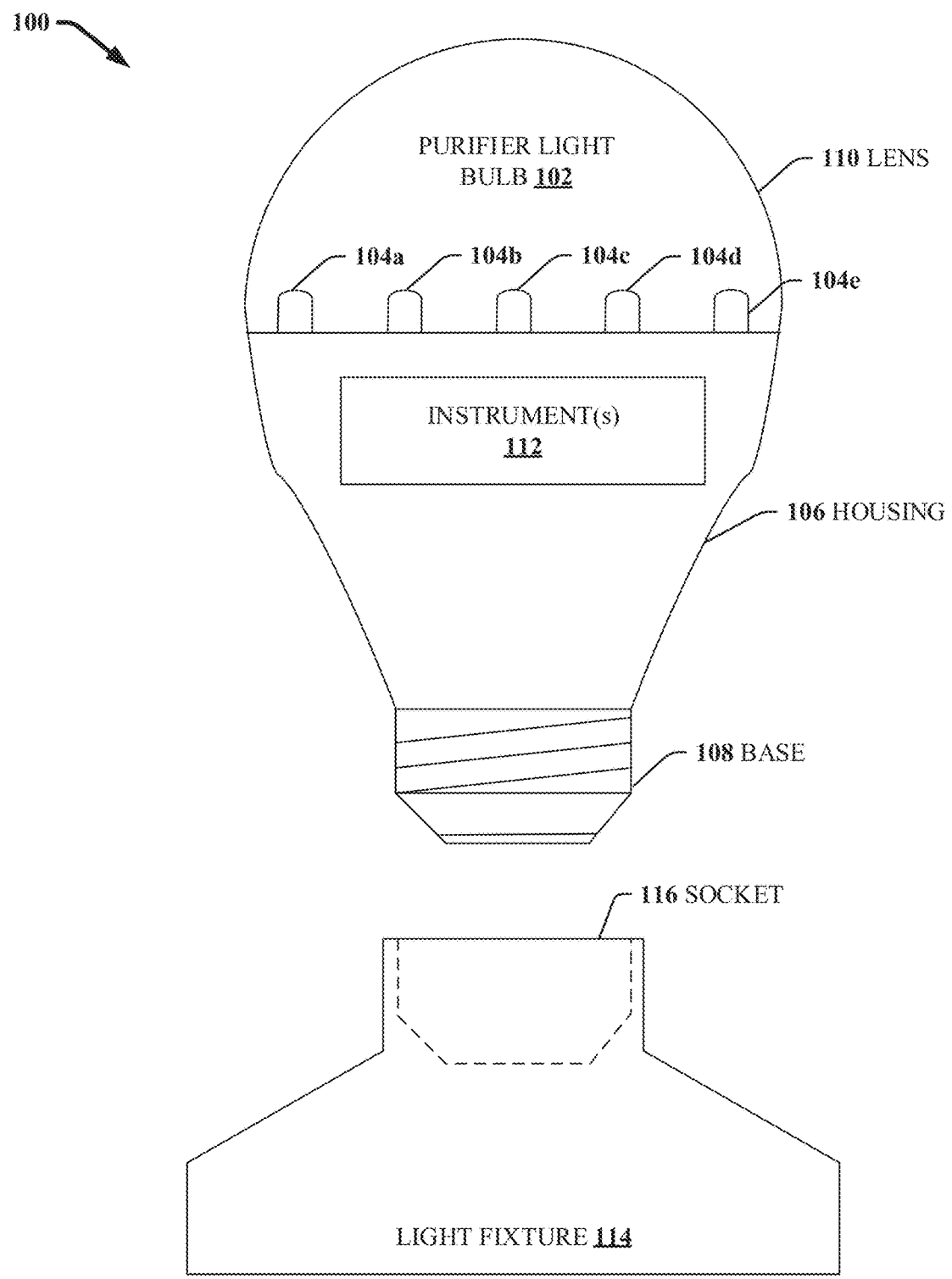
FIG. 1 illustrates a block diagram of an example, non-limiting purifier light in accordance with one or more embodiments described herein.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident; however in various cases, that the one or more embodiments can be practiced without these specific details.

Light has the ability to purify (e.g. clean, sanitize, disinfect, sterilize, decontaminate, deodorize, clarify, make hygienic, etc) many substances based on projection of particular electromagnetic characteristics (e.g. spectrum, wavelength, frequency, intensity, pattern, direction, etc.). For example, certain spectrums (e.g. UV, indigo, etc.) can neutralize contaminants (e.g. bacteria, mold, viruses, chemicals, particulates, etc.).

There is a need to provide intelligent purifier lights in various environments that can automatically identify purification needs of the environments and execute actions to purify the environments. It is to be appreciated that the environment can be an indoor environment, and outdoor environment, a liquid environment, an environment within a machine, or any other suitable environment in which a light can be installed.

In accordance with various disclosed aspects, a purifier light that comprises instruments, and is able to communicate with other purifier lights and other devices is presented. The purifier light can understand its environment and device ecosystem using the instruments, and perform a self-configuration to optimize its functionality to perform purification of the environment. In an example, the purifier light can employ artificial intelligence capabilities and instruments to monitor environmental conditions (e.g. air, surface, liquid, etc.) of the environment in which the purifier light is installed, and optimize function to purify the environment. For example, the purifier light can project a light output with defined electromagnetic characteristics that highlights contaminants, and use instrument 510 (e.g. camera, sensor, etc.) and pattern recognition to determine an unclean state (e.g. contamination level of contaminant above a defined unclean threshold). Based on determination of an unclean state, the purifier light can adjust light output (e.g. spectrum, wavelength, frequency, intensity, pattern, direction, etc.) to purify the environment of the contaminant (e.g. until contamination level of contaminant below a defined clean threshold). As a safety measure, the purifier light can monitor the environment for presence of humans/pets and delay purifying until the environment is devoid of humans/pets that might be negatively impacted by the purifying light output.

In an example, the purifier light can learn over time patterns of human/pet activity, contamination levels, and other conditions of an environment and adjust operations accordingly. The purifier light can adjust its lights, employ instruments, or instruct other devices/systems on operations to enhance purification of the environment while minimizing impact on humans/pets in the environment.

It is to be appreciated that the purifier light can be a retrofit light bulb with instruments integrated therein. In another embodiment, the purifier light can have all or a portion of the instruments integrated into a light fixture (e.g. socket, holder, ballast) for the purifier light. A purifier light can learn about its context and customize its configuration and/or operation in accordance with the context (e.g. using artificial intelligence). This can eliminate or minimize the need for an operator (e.g. user, administrator, or any other suitable entity) to perform manual configuration. Furthermore, a set of purifier lights can automatically perform coordinated self-configuration and operation. All examples below can involve coordination amongst a set of purifier lights to achieve an objective (e.g. goal, intention, purpose, action, operation, configuration, etc.), whether explicitly stated or not. Further, although the term "purifier light" is used herein, in various embodiments, the examples provided can include one or more purifier lights operating independently or in a distributed fashion, as applicable. All such embodiments are envisaged.

Figure 2:
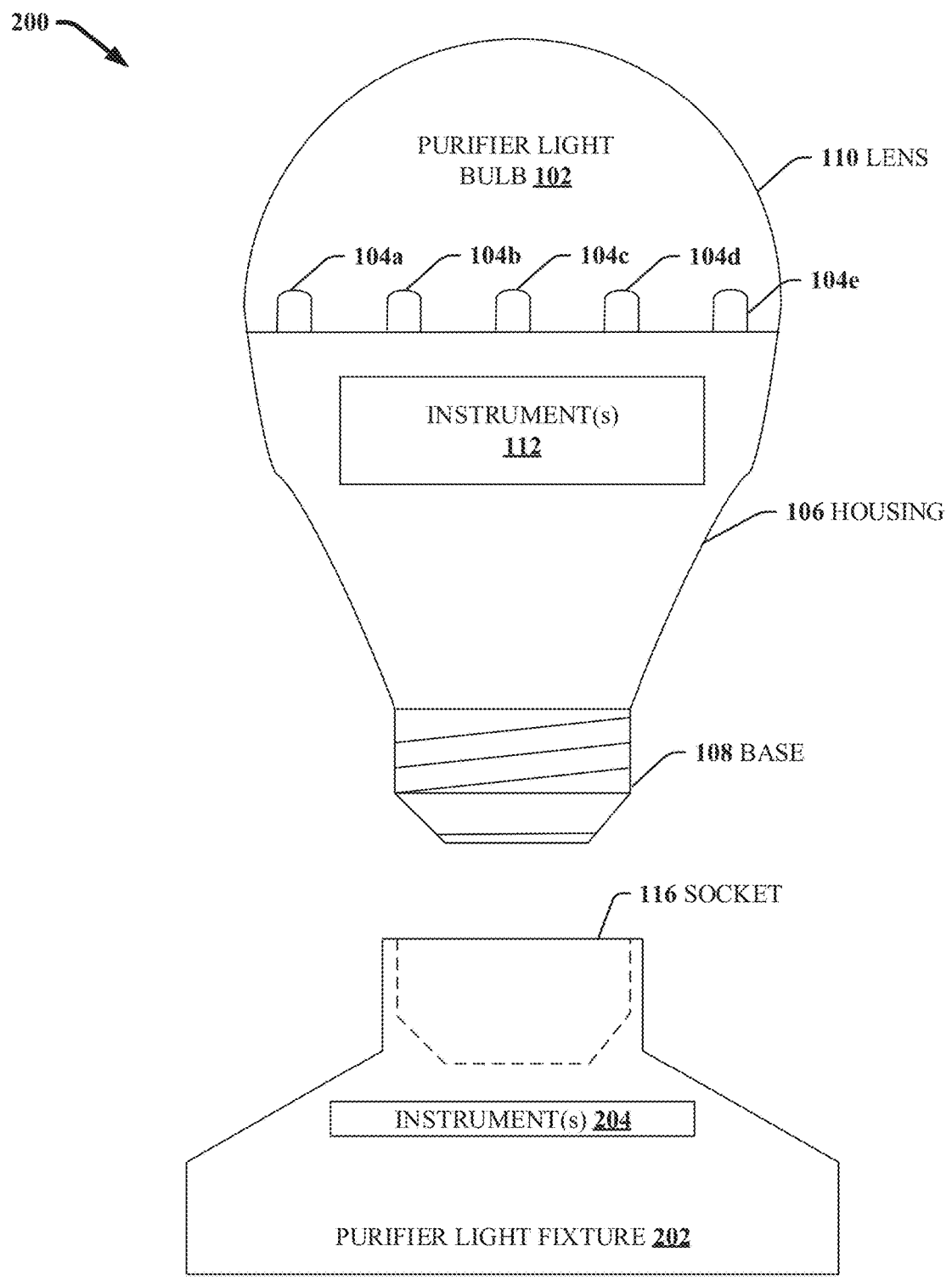
FIG. 2 illustrates a block diagram of an example, non-limiting purifier light in accordance with one or more embodiments described herein.

FIGS. 1-2 illustrate block diagrams of example, non-limiting purifier lights 100, 200 in accordance with one or more embodiments described herein. The subject disclosure is directed to computer processing systems, computer-implemented methods, apparatus and/or computer program products that facilitate efficiently, effectively, and automatically (e.g., with little or no direct involvement from an operator) employing purifier lights 100, 200 that perform self-configuration to identify contamination in an environment and utilize one or more instruments to perform one or more actions to purify the contamination from the environment. For example, when installed, purifier light 100, 200 can employ sensors, tools, and communication devices to determine its place in the environment and device ecosystem and perform an auto-configuration to perform purification functions in the environment. In an example, purifier light 100, 200 can employ sensors to understand the physical environment in which it is installed, and determine how it fits into the physical environment. In another example, purifier light 100, 200 can communicate on one or more networks to identify other purifier lights 100, 200 and other devices in the device ecosystem, and determine how it fits into the device ecosystem. Based on the determinations, purifier light 100, 200 can perform an autoconfiguration to perform purification functions in the environment. It is to be appreciated that a user interface (not shown) can be provided that allows an operator to manually adjust the configuration generated by the purifier light 100, 200.

In order to facilitate self-configuration, purifier lights 100, 200 described herein can be employed that are communicating with each other, communicating with another device. The purifier lights 100, 200 can coordinate amongst themselves to make decisions regarding actions to be taken by the purifier lights 100, 200. Purifier lights 100, 200 can receive instructions from another device, such as a control system, regarding actions to be taken by the purifier lights 100, 200. Purifier lights 100, 200 can receive instructions from an operator, regarding actions to be taken by the purifier lights 100, 200. A purifier light 100, 200 can autonomously make decisions regarding actions to be taken by the purifier light 100, 200. It is to be appreciated that purifier lights can employ any of the aforementioned decision-making methods, alone or in combination, regarding actions to be taken by the purifier lights 100, 200.

FIG. 1 illustrates a block diagram of an example, non-limiting purifier light 100 in accordance with one or more embodiments described herein. Purifier light 100 comprises a purifier light bulb 102 which can be installed as a retrofit into a socket 116 of conventional light fixture 114. Purifier light bulb 102 comprises one or more light emitting devices 104a, 104b, 104c, 104d, and 104e (e.g. light emitting diode (LED), organic light emitting diode (OLED), filament, quantum dot, incandescent, high-intensity discharge (HID), neon, fluorescent, compact fluorescent (CFL), electroluminescent (EL), laser, or any other suitable light emitting device) a housing 106, a base 108, a lens 110, and one or more instruments 112. It is to be appreciated that while five light emitting devices 104a, 104b, 104c, 104d, and 104e are depicted for illustrative purposes only, purifier light bulb 102 can include any suitable number of light emitting devices. It is also to be appreciated that purifier light bulb 102 can include other components (not shown) or exclude one or more components. For example, purifier light bulb 102 can exclude lens 110. In another example, purifier light bulb 102 can include one or more reflectors, one or more shades, one or more positioning motors, or any other suitable components needed according to functionality described herein.

FIG. 2 illustrates a block diagram of an example, non-limiting purifier light 200 in accordance with one or more embodiments described herein. Purifier light 100 comprises a purifier light bulb 102 which can be installed into a socket 116 of a purifier light fixture 202. Purifier light fixture 202 comprises one or more instruments 204. It is to be appreciated that purifier light fixture 202 can include other components (not shown) or exclude one or more components. For example, purifier light fixture 202 can include one or more light emitting devices, one or more reflectors, one or more shades, one or more positioning motors, or any other suitable components needed according to functionality described herein. It is to be appreciated that purifier light bulb 102 can communicate with purifier light fixture 202 via wired or wireless communications. For example, base 108 connecting to socket 116 can form a wired communication connection.

While FIGS. 1-2 depict a purifier light bulb 102 fitting into a light fixture 114, 202, it is to be appreciated that a single light fixture 114, 202 can comprise a plurality of sockets 116 for installation of a plurality of purifier light bulbs 102.

Figure 3:
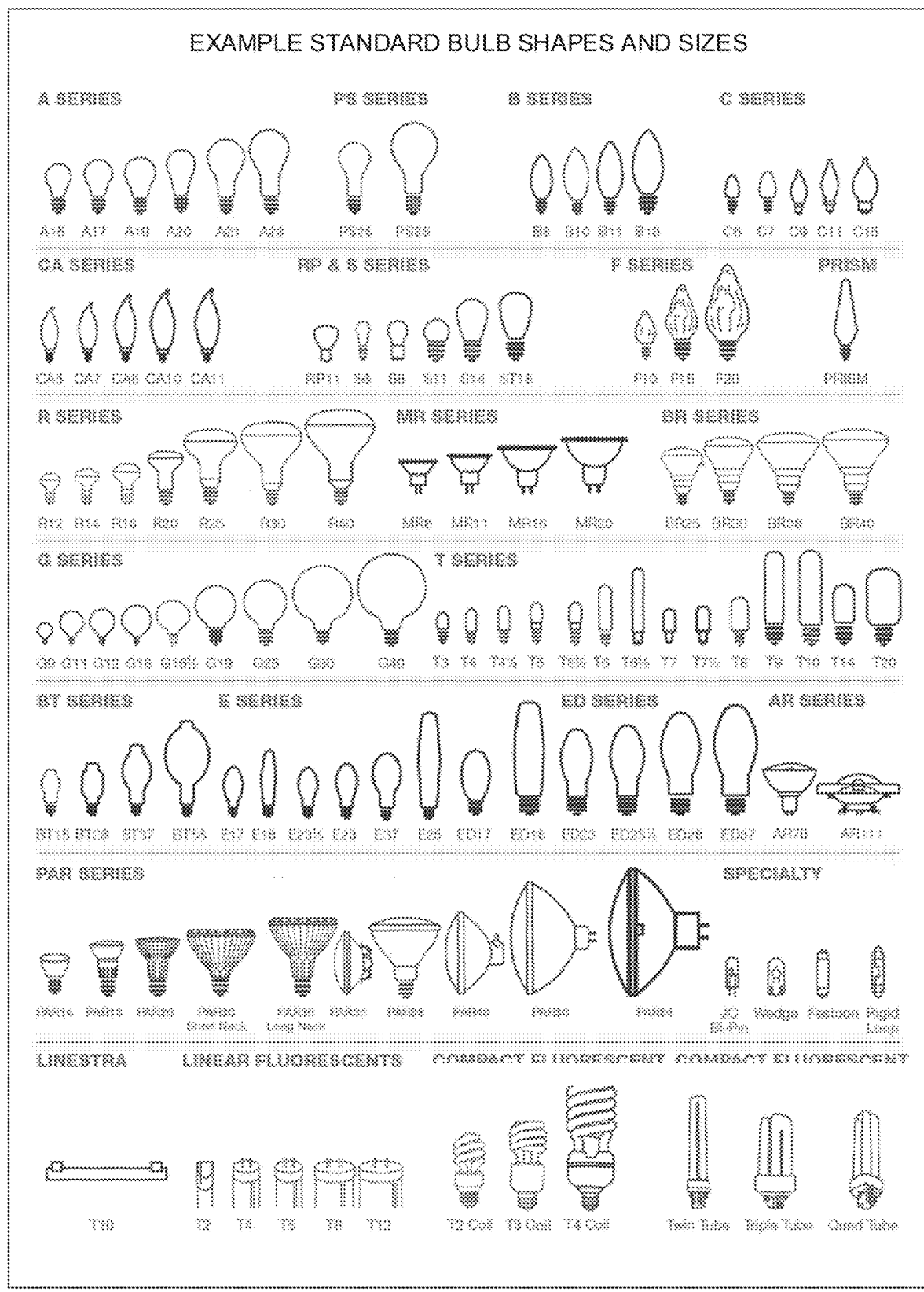
FIG. 3 illustrates example, non-limiting standard bulb shapes and size for purifier light bulb in accordance with one or more embodiments described herein.

FIG. 3 illustrates example, non-limiting standard bulb shapes and size for purifier light bulb 102. It is to be appreciated that purifier light bulb 102 can be customized to be in any suitable shape and any suitable size for an application in which purifier light bulb 102 is to be installed.

Figure 4:
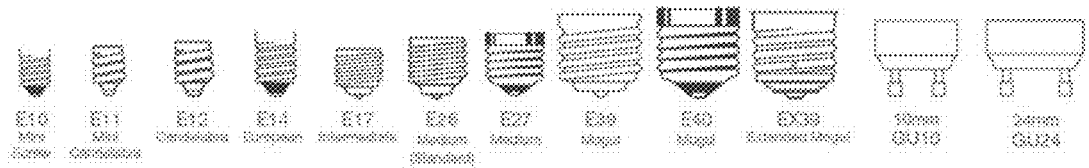
FIG. 4 illustrates example, non-limiting standard base types for base of purifier light bulb in accordance with one or more embodiments described herein.
Figure 4:
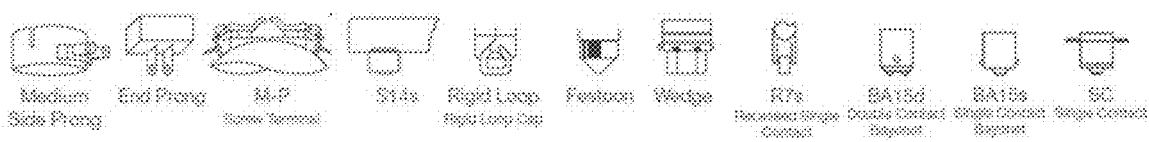
Figure 4:
Figure 4:
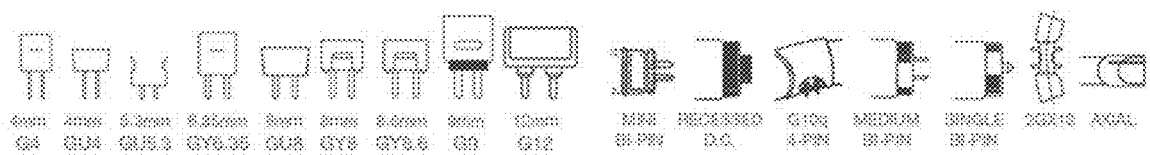
Figure 4:
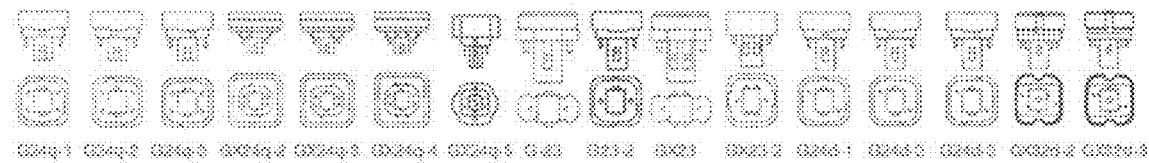
Figure 4:
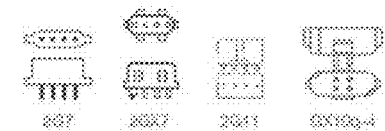

FIG. 4 illustrates example, non-limiting standard base types for base 108. It is to be appreciated that base 108 can be customized to be in any suitable form for an application in which purifier light bulb 102 is to be installed. Likewise, socket 116 can be customized to be compatible with base 108. Additionally, purifier light fixture 202 can be customized to be in any suitable form for an application in which purifier light 200 is to be installed.

A purifier light 100, 200 can include a power source, non-limiting examples of which include electrical grid power, battery, electrochemical cell, fuel cell, natural gas generated electric power, compressed air generated electric power, diesel fuel generated electric power, gasoline generated electric power, oil generated electric power, propane generated electric power, nuclear power system, solar power system, wind power system, piezoelectric power system, micro-electrical mechanical systems (MEMS)-generated electric power, inductive power system, radio-frequency power system, wireless power transfer mechanism, or any other suitable power source. In an example, a purifier light 100, 200 can have a constantly available power source, such as that provided by an electrical power grid. In another example, a purifier light 100, 200 can have a temporary power source, such as a battery (e.g. disposable battery or rechargeable battery). In a further example, a purifier light 100, 200 can generate and store its own power, such as by solar, fuel cell, radio-frequency harvesting, induction, piezoelectric, electro-mechanical, chemical, nuclear, carbon based-fuel, or any other suitable self-generating power source. This is advantageous for long-term installations (e.g. where frequent battery changes would be required) that do not have a constantly available power source, such as an outdoor environment where a power outlet is not available (e.g. a porch, a yard, a camping site, a farm field, a park, a sports field, etc.), or an indoor location where a power outlet is not available (e.g. a closet, a sunroom, a cabinet, a drawer, a garage, a barn, a shed, an indoor location where an extension cord is not desired, etc.). It is to be appreciated that purifier light 100, 200 can have a plurality of different power sources, with one or more power sources acting as a backup for another power source. It is to be appreciated that purifier light 100, 200 can have configurable power sources. For example, purifier light 100, 200 can have a modular configuration that allows for one or more power sources to be added or removed by a manufacturer or operator.

A purifier light 100, 200 can include one or more computers, one or more processors, one or more memories, and one or more programs. A purifier light 100, 200 can communicate via any suitable form of wireless or wired communication using a communication device. Non-limiting examples of wireless communication can include radio communication, optical communication, sonic communication, electromagnetic induction communication, or any other suitable wireless communication. A purifier light 100, 200 can include one or more instruments 112, 204, non-limiting examples of which include a communication device, a radio frequency identification (RFID) reader, a navigation device, a camera, a video camera, a three-dimensional camera, a global positioning system (GPS) device, a motion sensor, a radar device, a temperature sensor, a weather sensor, a humidity sensor, a barometer, a Doppler radar, a light sensor, a thermal imaging device, an infrared camera, an audio sensor, an ultrasound imaging device, a light detection and ranging (LIDAR) sensor, sound navigation and ranging (SONAR) device, a microwave sensor, a chemical sensor, a radiation sensor, an electromagnetic field sensor, a pressure sensor, a spectrum analyzer, a scent sensor, a moisture sensor, a biohazard sensor, a touch sensor, a gyroscope, an altimeter, a microscope, magnetometer, a device capable is seeing through or inside of objects, or any other suitable sensors. In addition, instruments 112, 204 can include tools, non-limiting examples of which include, a projectile launcher, a liquid sprayer, an air blower, a flame thrower, a heat projector, a cold projector, a scent projector, a chemical projector, an electric discharge device, a fire extinguisher, a laser, or any other suitable tools to perform any task. Additionally, instruments 112, 204 can include a display screen, a video projector, an audio speaker, or any other suitable instrument. It is to be appreciated that purifier light 100, 200 can have configurable instruments. For example, purifier light 100, 200 can have a modular configuration that allows for one or more instruments to be added or removed by a manufacturer or operator.

A purifier light 100, 200 can be constructed out of any suitable material appropriate for environments in which the purifier light 100, 200 will operate. A purifier light 100, 200 can have suitable protection against an environment in which the purifier light 100, 200 will operate, non-limiting examples of which include weather resistant, crush resistant, fire resistant, heat resistant, cold resistant, pressure resistant, impact resistant, liquid and/or solid material ingress protection, chemical resistant, corrosion resistant, shatter resistant, scratch resistant, bio-contamination resistant, electromagnetic pulse resistant, electrical shock resistant, projectile resistant, explosion resistant, or any other suitable resistance for an environment in which the purifier light 100, 200 will operate.

The computer processing systems, computer-implemented methods, apparatus and/or computer program products of purifier light 100, 200 employ hardware and/or software to solve problems that are highly technical in nature (e.g., related to complex coordination of one or more purifier lights 100, 200 possibly with other device to perform self-configuration of the one or more purifier lights 100, 200) that are not abstract and that cannot be performed as a set of mental acts by a human One or more embodiments of the subject computer processing systems, methods, apparatuses and/or computer program products enable one or more purifier lights 100, 200 to coordinate amongst themselves, and optionally with other devices, to perform actions to understand the environment in which the one or more purifier lights 100, 200 is installed, determine an objective of the installation, perform a self-configuration according to the determined objective, and operate to achieve the determined objective. For example, the purifier lights 100, 200 can employ artificial intelligence to learn their environment, and learn actions to perform to self-configure and operate for a determined objective of the installation in the environment.

Figure 5:
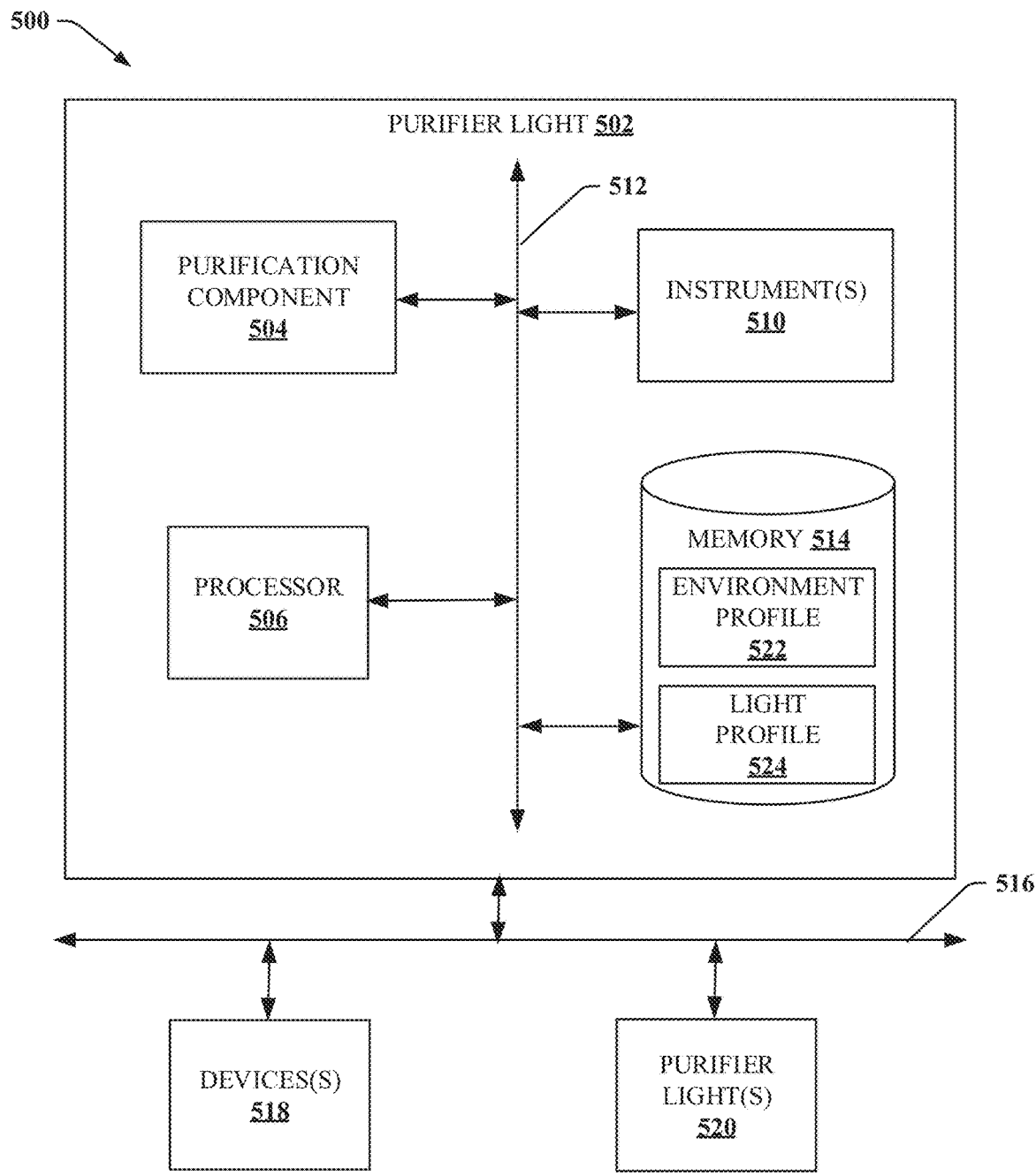
FIG. 5 illustrates a block diagram of an example, non-limiting purifier light in accordance with one or more embodiments described herein.

FIG. 5 illustrates a block diagram of an example, non-limiting system 500 that facilitates a purifier light 502 to understand the environment in which the purifier light 502 is installed, determine an objective of the installation, perform a self-configuration according to the determined objective, and operate to achieve the determined objective in accordance with one or more embodiments described herein. Repetitive description of like elements employed in other embodiments described herein is omitted for sake of brevity.

In some embodiments, the system 500 facilitates a plurality of purifier lights 502, 520 coordinating together to understand the environment in which the purifier lights 502, 520 are installed, determine an objective of the installation, perform a self-configuration related to purification of the environment according to the determined objective, and operate to achieve the determined objective in accordance with one or more embodiments described herein. Aspects of systems (e.g., system 500 and the like), apparatuses or processes explained in this disclosure can constitute machine-executable component(s) embodied within machine(s), e.g., embodied in one or more computer readable mediums (or media) associated with one or more machines. Such component(s), when executed by the one or more machines, e.g., one or more computers, one or more computing devices, one or more virtual machines, etc., can cause the one or more machines to perform the operations described.

As shown in FIG. 5, the system 500 can include purifier lights 502, 520, one or more networks 516, and one or more devices 518. In various embodiments, purifier lights 502, 520 can be or include the structure and/or functionality of one or more of purifier lights 100 or 200 and/or any other structure and/or functionality described herein for purifier lights. In one example, purifier light 502 can be a different type of purifier light than purifier light 520. In another example, a purifier light 520 can be a purifier light 502 and/or include one or more components of purifier light 502. It is to be appreciated that in disclosure herein in which more than one purifier light is employed, the purifier lights can include one or more purifier light 502 and/or one or more purifier light 520.

Purifier light 502 can include instruments 510, which can include or be one or more of numerous different types of instruments 112, 204 disclosed herein. Purifier light 502 can communicate with other purifier lights 520 and devices 518 over one or more networks 516 via wireless and/or wired communications using instruments 510. Purifier light 502 can include purification component 504 that can enable purifier light 502 to understand the environment in which the purifier light 502 is installed, determine an objective of the installation, perform a self-configuration related to purification of the environment according to the determined objective, and operate to achieve the determined objective.

Purifier light 502 can include or otherwise be associated with at least one memory 514 that can store computer executable components (e.g., computer executable components can include, but are not limited to, the purification component 504, and/or associated components) and can store any data generated or obtained by purifier light 502 and associated components. Memory 514 can store an environment profile 522 that describes characteristics of an environment in which purifier light 502 is installed. Memory 514 can store a light profile 524 that can include environment profile, and capabilities and configuration of purifier light 502. Purifier light 502 can also include or otherwise be associated with at least one processor 506 that executes the computer executable components stored in the memory 514. Purifier light 502 can further include a system bus 512 that can couple the various components including, but not limited to, purification component 504, instruments 510, memory 514, processor 506, and/or other components.

Device 518 can be any electronic device that can electronically interact (e.g. unidirectional interaction or bidirectional interaction) with purifier light 502, non-limiting examples of which can include a wearable electronic device or a non-wearable electronic device. It is to be appreciated that interaction can include in a non-limiting example, communication, control, physical interaction, or any other suitable interaction between devices. Wearable device can include, for example, heads-up display glasses, a monocle, eyeglasses, contact lens, sunglasses, a headset, a visor, a cap, a mask, a headband, clothing, or any other suitable device that can be worn by a human or non-human user that comprises electronic components. Non-wearable devices can include, for example, a system (e.g. temperature, humidity, insect repellent, sound, air flow, air quality, windows, robots, or any other suitable systems associated with an environment), a mobile device, a mobile phone, a camera, a camcorder, a video camera, laptop computer, tablet device, desktop computer, server system, cable set top box, satellite set top box, cable modem, television set, monitor, media extender device, blu-ray device, DVD (digital versatile disc or digital video disc) device, compact disc device, video game system, portable video game console, audio/video receiver, radio device, portable music player, navigation system, car stereo, a mainframe computer, a robotic device, an artificial intelligence system, a home automation system, a security system, a messaging system, a presentation system, a sound system, a warning system, a fire suppression system, a lighting system, a network storage device, a communication device, a web server device, a network switching device, a network routing device, a gateway device, a network hub device, a network bridge device, a control system, or any other suitable device. Device 518 can be equipped with a communication device that enables device 518 to communicate with purifier light 502 and/or 520 over network 516. It is to be appreciated that a device 518 can be employed by an operator to interact with a purifier light 502 and/or 520.

The various components (e.g., purification component 504, instruments 510, memory 514, processor 506, purifier lights 502, 520, and/or other components) of system 500 can be connected either directly or via one or more networks 516. Such networks 516 can include wired and wireless networks, including, but not limited to, a cellular network, a wide area network (WAN) (e.g., the Internet), or a local area network (LAN), non-limiting examples of which include cellular, WAN, wireless fidelity (Wi-Fi), Wi-Max, WLAN, radio communication, microwave communication, satellite communication, optical communication, sonic communication, electromagnetic induction communication, or any other suitable communication technology.

Figure 6:
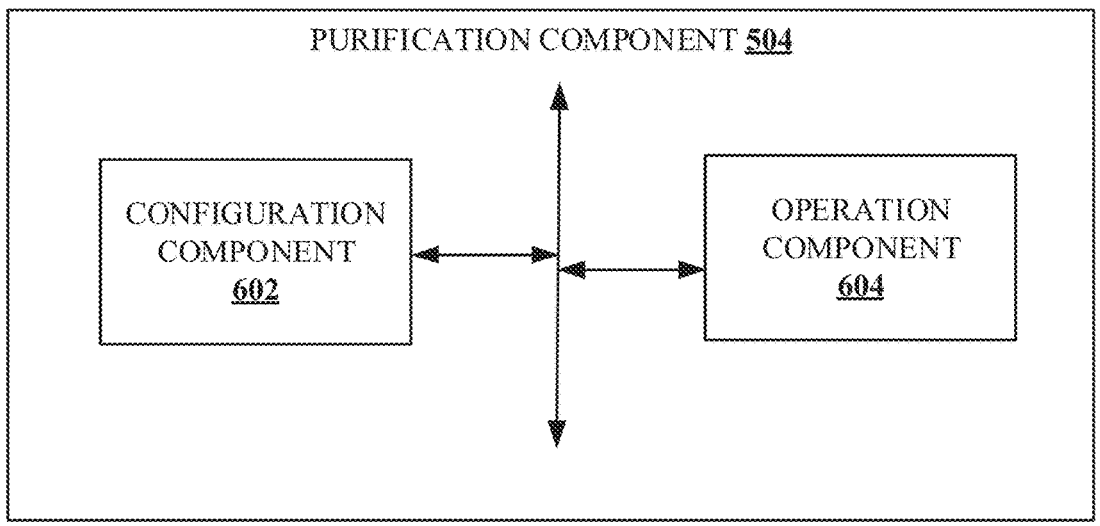
FIG. 6 illustrates a block diagram of an example, non-limiting purification component in accordance with one or more embodiments described herein.

FIG. 6 illustrates a block diagram of an example, non-limiting purification component 504 that can facilitate purifier light 502 to determine (e.g., ascertain, infer, calculate, predict, prognose, estimate, derive, forecast, detect, and/or compute) characteristics of the environment in which the purifier light 502 is installed, determine capabilities of purifier light 502, determine one or more objectives of the installation of purifier light 502, perform a self-configuration of purifier light 502 related to purification of the environment according to the determined one or more objectives, and determine and execute suitable actions for purifier light 502 to perform to achieve the determined one or more objectives in accordance with one or more embodiments described herein. Repetitive description of like elements employed in other embodiments described herein is omitted for sake of brevity.

Purification component 504 can include configuration component 602 that can determine characteristics of an environment in which the purifier light 502 is installed, determine capabilities of purifier light 502, determine one or more objectives of the installation of purifier light 502, and perform a self-configuration of purifier light 502 related to purification of the environment according to the determined one or more objectives. Purification component 504 can also include operation component 604 that can monitor characteristics of environment over time, for example, as they relate to purification of the environment, and determine and execute suitable actions for purifier light 502 to perform to achieve the determined one or more objectives related to purification of the environment.

Configuration component 602 can employ one or more instruments 510 to obtain information about the environment in which the purifier light 502 is installed and determine characteristics of the environment. In a non-limiting embodiment, characteristics can include objects, devices, people, flora, fauna, predators, pests, contaminations, colors, scents, biohazards, chemicals, dimensional characteristics, health status, locations, topography, landscape, seascape, boundaries, atmosphere, manmade features, furniture, toys, equipment, machines, vehicles, buildings, grounds, roads, railroad tracks, water feature, rocks, trees, debris, geographic features, unsafe conditions, weather conditions, property line boundary, ground conditions, water conditions, atmospheric conditions, water currents, air currents, water salinity, air temperature, water temperature, ground temperature, ground traction, network topology, or any other suitable characteristics of the environment that can be determined from information obtained by instruments 510.

It is to be appreciated that configuration component 602 can employ intelligent recognition techniques (e.g., spatial relationship recognition, pattern recognition, object recognition, facial recognition, animal recognition, pose recognition, action recognition, shape recognition, scene recognition, behavior recognition, sound recognition, scent recognition, voice recognition, audio recognition, image recognition, motion recognition, hue recognition, feature recognition, edge recognition, texture recognition, timing recognition, location recognition, and/or any other suitable recognition technique) to determine characteristics based on information obtained by one or more instruments 510.

Configuration component 602 can employ one or more sensors as described above to obtain physical information about the physical environment in which purifier light 502 is installed. In an example, configuration component 602 can employ a camera to obtain visual information about the environment. In another example, configuration component 602 can employ a microphone to obtain audio information about the environment. In a further example, configuration component 602 can employ a GPS device to obtain its location in the environment. In another example, configuration component 602 can employ an LIDAR sensor to obtain mapping information about the environment. In an additional example, configuration component 602 can employ GPS device and LIDAR sensor to map the locations of characteristics recognized in the environment. It is to be appreciated that configuration component 602 can employ any suitable instrument to obtain corresponding information produced by the instrument about the physical environment.

Configuration component 602 can also employ one or more instruments as described above to obtain information about the network environment in which purifier light 502 is installed. In an example, configuration component 602 can employ a communication device to discover communication networks operating in the environment. Configuration component 602 can connect to one or more of the networks using suitable security and authentication schemes and obtain device information about devices 518 and/or purifier lights 520 operating on the networks. In a non-limiting example, device information can comprise device type, device model number, device location, device functionality, device configuration, device security, communication protocols supported, or any other suitable attribute of a device 518. It is to be appreciated that configuration component 602 can employ suitable security techniques to prevent unauthorized access to purifier light 502 while obtaining device information on other devices 118 on the one or more networks. Purifier light 502 can determine what security and/or communication protocols it should employ and self-configure for operation using the appropriate security and/or communication protocols.

Configuration component 602 can create an environment profile 522 that describes the characteristics of the environment in which purifier light 502 is installed based on the physical information and the device information obtained by the one or more instruments 510. For example, configuration component 602 can employ intelligent recognition techniques to recognize characteristics of the environment based on the physical information and the device information. In an additional example, configuration component 602 can associate device information obtained from devices 518 with corresponding physical information associated with the devices 518 obtained from sensors. Configuration component 602 can also employ knowledge resources (e.g., internet, libraries, encyclopedias, databases, devices 518, or any other suitable knowledge resources) to obtain detailed information describing the characteristics. For example, configuration component 602 can obtain detailed product information related to recognized characteristics of the environment. In another example, configuration component 602 can obtain risk information related to recognized characteristics of the environment. In a further example, configuration component 602 can obtain information describing interaction between various recognized characteristics of the environment. Configuration component 602 can obtain any suitable information associated with recognized characteristics of the environment from any suitable knowledge resource.

Furthermore, configuration component 602 can generate a confidence metric indicative of a confidence of a determination of a characteristic that has been made by configuration component 602 based on any suitable function. For example, configuration component 602 can employ the multiple sources of information (e.g., physical information, device information, and information from knowledge sources) and perform a cross-check validation across the various sources to generate a confidence metric indicative of a confidence of an accuracy of a determination of a characteristic.

Configuration component 602 can employ the characteristics and any associated obtained information to generate an environment profile 522 that describes the characteristics of the environment. The environment profile 522 can be organized in any suitable manner, non-limiting examples of which include an array, a table, a tree, a map, graph, a chart, a list, network topology, or any other suitable manner of organizing data in a profile. In a non-limiting example, environment profile 522 can include respective entries for each characteristic of the environment that comprise a detailed description of the characteristic, a location of the characteristic in the environment, tracking information describing changes to the characteristic over time, source used to determine the characteristic, confidence of accuracy of the determined characteristic, or any other suitable information associated with the characteristic. Environment profile 522 can include a map of the environment identifying characteristics and their locations on the map.

Figure 7A:
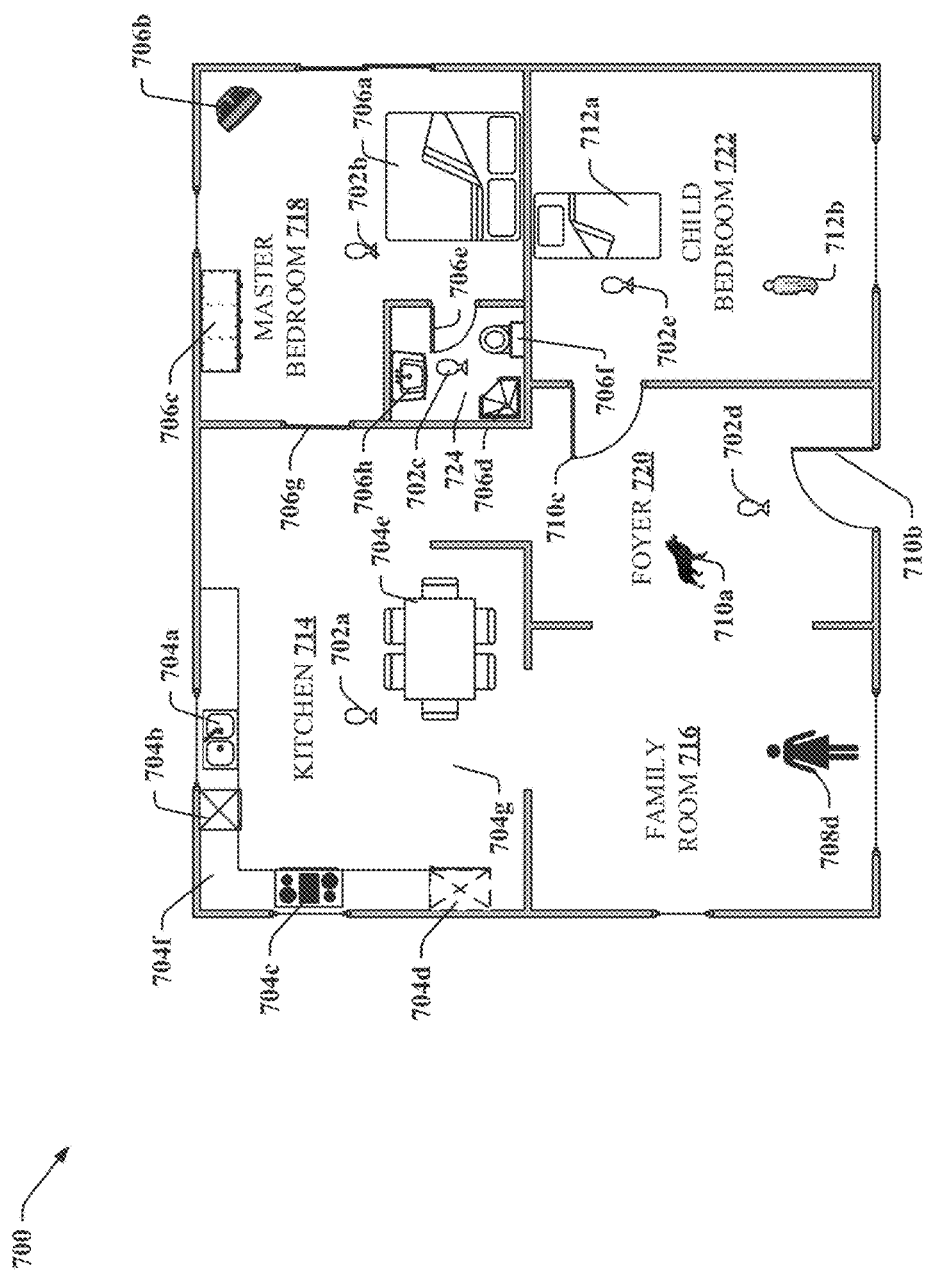
FIGS. 7A and 7B illustrate a block diagram of an example, non-limiting environment in which purifier lights are installed in accordance with one or more embodiments described herein.

FIG. 7A illustrates a block diagram of an example, non-limiting environment 700 in which purifier lights are installed in accordance with one or more embodiments described herein. For exemplary purposes only, environment 700 is depicted as a home. It is to be appreciated that purifier lights can be installed in any suitable environment, non-limiting examples of which can include indoor, outdoor, liquid, gaseous, embedded in a material, building, office, hospital, laboratory, surgical room, bathroom, kitchen, bedroom, refrigerator, faucet, bed, oven, microwave, factory, warehouse, school, mall, store, bus terminal, train terminal, airport, vehicle, device, machine, or any other suitable environment. All such embodiments are envisaged.

Environment 700 has installed purifier lights 702a, 702b, 702c, 702d, and 702e which can respectively be or include portions of purifier light 502. While FIG. 7A depicts five purifier lights for exemplary purposes, it is to be appreciated that any suitable quantity of purifier lights can be installed in an environment.

Purifier light 702a can employ instruments 510 to determine characteristics of the environment 700 in which it is installed. For example, purifier light 702a can employ instruments 510 to obtain physical information by recognizing characteristics, such as sink 704a, dishwasher 704b, stove 704c, refrigerator 704d, dining table 704e, counter 704f, door 706g, and woman 708d. In a further example, purifier light 702a can determine atmospheric conditions, scents, allergens, contaminations, cleaning chemicals used, lighting conditions at various times of the day, usage of characteristics over time, dimensional information of the characteristics, locations of characteristics, traffic in the environment, changes to characteristics over time, or any other suitable physical information that can be obtained from instruments 510. Additionally, purifier light 702a can determine that it is located near the center of a room. In another example, purifier light 702a can employ communication devices to determine and establish communications on networks (e.g. Wi-Fi, home automation, etc.), such as a network on which devices dishwasher 704b, stove 704c, and refrigerator 704d are communicating and obtain device information from devices dishwasher 704b, stove 704c, and refrigerator 704d. Purifier light 702a can also communicate with one or more knowledge sources to obtain information about characteristics of the environment. It is to be appreciated that purifier light 702a can also establish a direct communication link (e.g., not through a network) with a device 118 to obtain device information. Purifier light 702a can also establish communications with one or more of purifier lights 702b, 702c, 702d, or 702e and obtain information about environment 700 that those purifier lights have determined. Purifier light 702a can determine based on the information (e.g. physical information, device information, and/or information from knowledge sources) that purifier light 702a is installed in an environment that is kitchen 714. Furthermore, purifier light 702a can determine that it is part of a larger environment 700 that is a home based on the information. Purifier light 702a can generate an environment profile 522 for purifier light 702a based on the determined characteristics and associated obtained information.

Furthermore, purifier lights 702b, 702c, 702d, and 702e can employ instruments 510 to physical information, such as characteristics of the environment 700 in which it is installed. For example, purifier light 702b can recognize characteristics, such as king size bed 706a, television 706b, dresser 706c, door 706e, and door 706g, and determine that purifier light 702b is installed in an environment that is master bedroom 718. In another example, purifier light 702b can recognize characteristics, such as sink 706h, shower 706d, toilet 706f, and door 706e, and determine that purifier light 702c is installed in an environment that is bathroom 724. In an additional example, purifier light 702d can recognize characteristics, such as dog 710a, front door 710b, and door 710c, and determine that purifier light 702d is installed in an environment that is foyer 720. In a further example, purifier light 702e can recognize characteristics, such as bed 712a, child 712b, and door 710c, and determine that purifier light 702e is installed in an environment that is child bedroom 722. Furthermore, purifier lights 702b, 702c, 702d, and 702e can determine atmospheric conditions, scents, allergens, contaminations, cleaning chemicals used, lighting conditions at various times of the day, usage of characteristics over time, dimensional information of the characteristics, locations of characteristics, traffic in the environment, changes to characteristics over time, or any other suitable physical information that can be obtained from instruments 510. One or more of purifier lights 702a, 702b, 702c, 702d, and 702e can communicate with each other to obtain information about environment 700 that those purifier lights have determined.

Referring back to FIG. 6, configuration component 602 can determine capabilities, such as in a non-limiting example, power sources, computers, processors 506, memories 514, programs, instruments 112, 204, or any other suitable capability of purifier light 502. In an example, configuration component 602 can probe system bus 512 to determine capabilities of purifier light 502. In another example, configuration component 602 can examine memory 514 for information on capabilities of purifier light 502. In a further example, configuration component 602 can obtain information on capabilities of purifier light 502 from one or more knowledge sources. It is to be appreciated that configuration component 602 can employ any suitable mechanism to determine capabilities of purifier light 502.

Configuration component 602 can also determine one or more objectives of the installation of purifier light 502. For example, configuration component 602 can employ artificial intelligence to determine an objective of the installation of purifier light 502 based on environment profile 522 and determined capabilities of purifier light 502. In a non-limiting example, an objective can be related to maintaining purification, safety, automation, control, communication, economics, activity enhancement, notification, coordination, monitoring, intervention, time management, workflow management, or any other suitable objective related to purification of the environment. For example, an objective can be related to minimizing usage of chemicals to satisfy a cleanliness criterion of the environment. In another example, an objective can be to minimize cost to satisfy a cleanliness criterion. In a further example, an objective can be to minimize manual labor to satisfy a cleanliness criterion. In another example, an objective can be to balance one or more criterion according to a utility analysis (e.g. cost versus benefit). In an additional example, an objective can be to minimize interruption to activities of a set of humans in the environment while satisfying a cleanliness criterion. Furthermore, a plurality of purifier lights 502 can coordinate to determine common objectives. It is to be appreciated that any suitable objective can be determined for the environment.

In an example, configuration component 602 can select objectives from a library of objectives stored in memory 514 or in one or more knowledges sources. In another example, configuration component 602 can create objectives based on artificial intelligence. In a further example, configuration component 602 can create linked objectives, wherein one or more objectives depends on one or more other objectives. For example, an objective can become active if another objective is achieved. In another example, an objective can become inactive if another objective is achieved. It is to be appreciated that configuration component 602 can employ any suitable mechanism to determine objectives of purifier light 502. In a further example, objectives can be defined by an operator.

It is to be appreciated that cleanliness criterion can be related to any suitable criterion for level of a contamination using any suitable measurement scale. For example, cleanliness can relate to contamination, such as germs, pathogen, bacteria, virus, mold, fungus, toxins, pests, dirt, waste, odors, allergens, gases, liquids, solids, hazardous materials, sewage, radiation, chemical, biological, physical, or any other suitable type of contamination. Furthermore any suitable threshold can be defined for determination of whether a level of a contamination satisfies a cleanliness criterion.

Configuration component 602 can also generate a light profile 524 for purifier light 502 according to the determined one or more objectives. Light profile 524 can comprise environment profile 522 for purifier light 502, capabilities of purifier light 502, and objectives of purifier light 502. Light profile 524 can be organized in any suitable manner, non-limiting examples of which include an array, a table, a tree, a map, graph, a chart, a list, topology, or any other suitable manner of organizing data in a profile. In a non-limiting example, light profile 524 can include respective entries for each objective that comprise a detailed description of the objective, success metrics for the objective, tracking information describing changes to the objective over time, source used to determine the objective, confidence of accuracy of the determined objective, or any other suitable information associated with the objective. Furthermore, configuration component 602 can configure settings of one or more parameters of purifier light 502 (e.g., of processors, memory, programs, instruments 510, purifier light bulb 102, purifier light fixture 202, housing 106, lens 110, light emitting devices, base 108, socket 116, or any other suitable parameters of components of purifier lights 502) to achieve the one or more objectives, and store the settings in light profile 524.

Referring back to FIG. 6, purification component 504 can include operation component 604 that can determine and execute suitable actions for purifier light 502 to perform to achieve the determined one or more objectives. For example, operation component 604 can employ artificial intelligence to monitor the environment for conditions of the characteristics according to the determined one or more objectives using instruments 510, determine one or more suitable actions for purifier light 502 to perform to achieve the determined one or more objectives based on the conditions of the characteristics and the determined capabilities, and execute the one or more suitable actions. In an example, operation component 604 can select actions from a library of actions stored in memory 514 or in one or more knowledges sources. In another example, operation component 604 can create actions to perform based on artificial intelligence.

In another example, an operator can employ a user interface (not shown) of an application on a device 518 to enter information overriding data in environment profile 522, light profile 524, and/or actions determined by purifier light 502.

Referring to FIG. 7A again, configuration component 602 of purifier light 702a can determine purification objectives associated with kitchen 714. For example, purifier light 702a can determine an objective to have counter 704f satisfy a first cleanliness criterion and floor 704g at a second cleanliness criterion. Since counter 704f can be used for food preparation the first cleanliness criterion can be higher than the second cleanliness criterion. In another example, purifier light 702a can determine an objective to have table 704e also satisfy the first cleanliness criterion since it can be used for eating. In a further example, purifier light 702a can determine an objective of having air in the kitchen satisfy a particular cleanliness criterion associated with an amount of smoke in the air. Operation component 604 of purifier light 702a can employ instruments 510 to monitor counter 704f, floor 704g, table 704e, and air of kitchen 714 for one or more contaminants and their associated level of contamination. For example, purifier light 702a can project a light output with defined electromagnetic characteristics that highlights a contaminant for a particular instrument 510 to detect a level of contamination associated with the contaminant. In another example, purifier light 702a can capture air from kitchen 714 and employ an instrument 510 to perform an analysis on the air to determine a contaminant and its associated level of contamination. Operation component 604 of purifier light 702a can determine an action to perform in response to a contaminant not satisfying a cleanliness criterion associated with the contaminant. For example, if a contaminant on counter 704f does not satisfy the first cleanliness criterion, purifier light 702a can take an action to try to make the contaminant satisfy the first cleanliness criterion. In an example, purifier light 702a can project a light output with defined electromagnetic characteristics that can reduce the contaminant to satisfy the first cleanliness criterion. In another example, purifier light 702a can employ an instrument 510 reduce the contaminant to satisfy the first cleanliness criterion, such as spraying a cleaner on counter 704f. In a further example, purifier light 702a can provide a notification to woman 708*d* that counter 704*f* has a contaminant that does not satisfy the first cleanliness criterion.

In another example, if a contaminant on floor 704*g* does not satisfy the second cleanliness criterion, purifier light 702*a* can take an action to try to make the contaminant satisfy the second cleanliness criterion. For example, purifier light 702*a* can control a robotic floor mop/vacuum to clean floor 704*g*. In a further example, if a contaminant, such as smoke or pathogen, in the air of kitchen 714 does not satisfy a defined cleanliness criterion, purifier light 702*a* can employ an instrument 510, such as an air filter to try to reduce the contaminant to satisfy the defined cleanliness criterion.

In an additional example, purifier light 702*b* can determine an objective of have king size bed 706*a* satisfy the defined cleanliness criterion, such as related to a contaminant of bedding on king size bed 706*a*. Purifier light 702*b* can project a light output and/or employ an instrument 510 to detect a level of contamination associated with the contaminant on bedding on king size bed 706*a*. If the contaminant on bedding of king size bed 706*a* does not satisfy the defined cleanliness criterion, purifier light 702*b* can take an action, such as projecting a light output, employing an instrument 510, controlling a device 118, or providing a notification to a device 118 to try to make the contaminant satisfy the defined cleanliness criterion. For example, if purifier light 702*b* determines that a contaminant such as bed bugs are on the bedding of king size bed 706*a*, purifier light 702*b* can project a light output with defined electromagnetic characteristics that kills or drives away bed bugs. In another example, purifier light 702*b* can spray a chemical that kills or drives away bed bugs.

If a further example, purifier light 702*c* can determine an objective of having sink 706*h*, shower 706*d*, and/or toilet 706*f* satisfy the defined cleanliness criterion, such as related to their surfaces. Purifier light 702*c* can project a light output and/or employ an instrument 510 to detect a level of contamination associated with a contaminant on a surface of sink 706*h*, shower 706*d*, and/or toilet 706*f*. If the contaminant on a surface of sink 706*h*, shower 706*d*, and/or toilet 706*f* does not satisfy the defined cleanliness criterion, purifier light 702*c* can take an action, such as projecting a light output, employing an instrument 510, controlling a device 118, or providing a notification to a device 118 to try to make the contaminant satisfy the defined cleanliness criterion. For example, if purifier light 702*c* determines that a contaminant, such a pathogen, on a surface of sink 706*h*, shower 706*d*, and/or toilet 706*f*, does not satisfy the defined cleanliness criterion, purifier light 702*b* can project a light output with defined electromagnetic characteristics that kills the pathogen until the contaminant satisfy the defined cleanliness criterion. In another example, purifier light 702*c* can provide a notification to woman 708*d*, that the pathogen exists on the surface of sink 706*h*, shower 706*d*, and/or toilet 706*f* so they can take action to determine if they have been infected by the pathogen. In a further example, purifier light 702*c* can instruct purifier light 702*a*, 702*b*, 702*d*, and/or 702*e* to employ instruments 510 to determine if the pathogen is on woman 708*d*, child 712*b*, and/or dog 710*a*, and provide a notification to woman 708*d* if the pathogen is detected on woman 708*d*, child 712*b*, and/or dog 710*a*.

In another example, purifier light 702*c* can determine an objective of having air in foyer 720 satisfy the defined cleanliness criterion, such as related to odors in foyer 720, for example from dog 710*a*. Purifier light 702*d* can capture air from foyer 720 and employ an instrument 510 to perform an analysis on the air to determine a contaminant, such as an odor, and its associated level of contamination. If purifier light 702*d* determines that the odor does not satisfy the defined cleanliness criterion, purifier light 702*d* can perform an action to mitigate the odor, such as spraying a scent or chemical to neutralize the odor. It is to be appreciated that purifier light 702*d* can determine that dog 710*a* is present in foyer 720 and not perform an action that could be harmful to dog 710*a*.

In another example, purifier light 702*e* can determine an objective of having the child bedroom 722 satisfy a defined cleanliness criterion, such as related to allergens in the air of child bedroom 722 due to allergies of child 712*b*. Purifier light 702*c* can capture air from child bedroom 722 and employ an instrument 510 to perform an analysis on the air to determine a contaminant, such as an allergen, and its associated level of contamination. If purifier light 702*c* determines that the allergen does not satisfy the defined cleanliness criterion, purifier light 702*c* can perform an action to mitigate the odor, such as controlling a heating, ventilation, and air conditioning (HVAC) system to filter the air in child bedroom 722. In an additional example, purifier light 702*c* controlling HVAC to lower temperature can reduce mold from growing. In a further example, purifier light 702*c* controlling HVAC to lower humidity can reduce dust mites. It is to be appreciated that purifier light 702*e* can determine that child 712*b* is present in child bedroom 722 and not perform an action that could be harmful to child 712*b*.

Figure 7B:
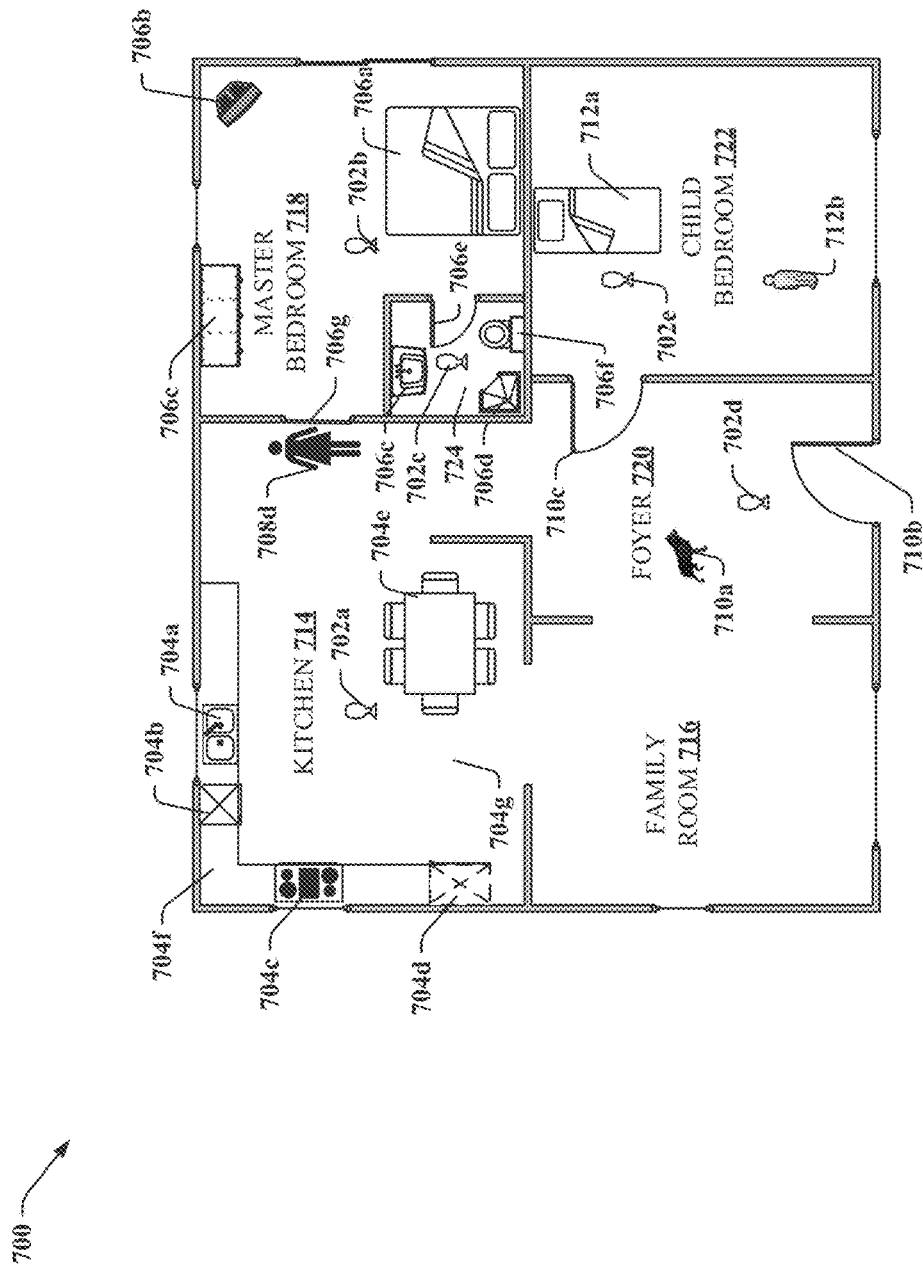

FIG. 7B illustrates a block diagram of an example, non-limiting environment 700 in which purifier lights are installed in accordance with one or more embodiments described herein. In FIG. 7B, woman 708*d* is approaching door 706*g*. Purifier light 702*b* can receive notification from purifier light 702*a* and/or 702*d* that woman 708*d* is approaching door 706*g*, and stop any purification actions being performed in master bedroom 718 that could have a harmful effect on woman 708*d* if woman 708*d* enters master bedroom 718. In an example, purifier light 702*b* can monitor door 706*g* an upon detecting door 706*g* opening, and stop any purification actions being performed in master bedroom 718 that could have a harmful effect on woman 708*d*. In an example, purifier light 702*b* can stop any purification actions being performed in master bedroom 718 that could have a harmful effect on woman 708*d* upon receiving the notification from purifier light 702*a* and/or 702*d*.

Figure 8:
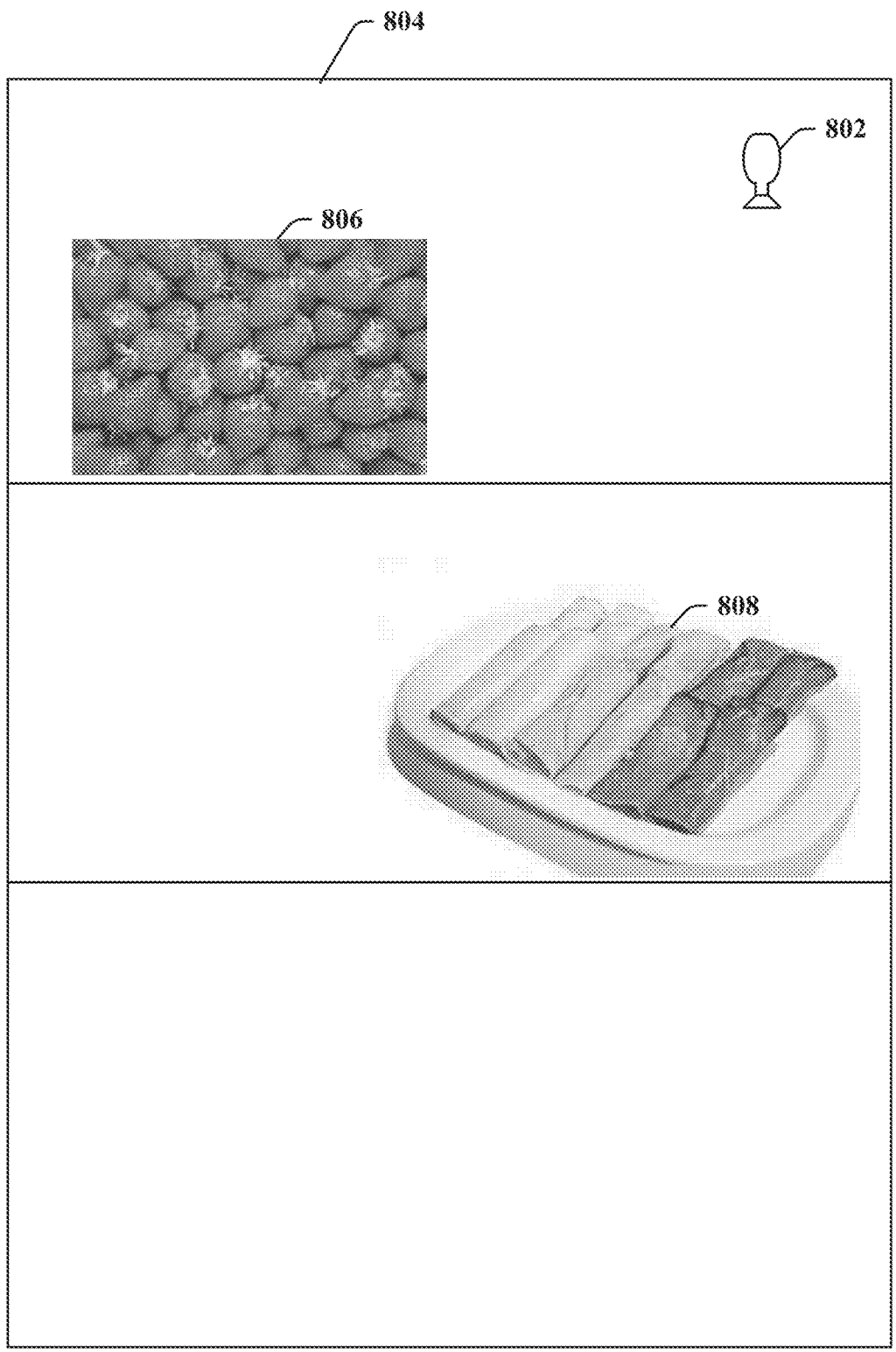
FIG. 8 illustrates a block diagram of an example, non-limiting environment in which a purifier light is installed in accordance with one or more embodiments described herein.

FIG. 8 illustrates a block diagram of an example, non-limiting refrigerator 804 in which purifier light 802 is installed in accordance with one or more embodiments described herein. Purifier light 802 can be or include portions of purifier light 502. For example, purifier light 502 can be purifier light bulb 102 installed as a retrofit into a light fixture 114 in refrigerator 804. In another example, purifier light 502 can be purifier light 200 where purifier light fixture 202 replaces a light fixture 114 in refrigerator 804 and has purifier light bulb 102 installed. Refrigerator 804 can include strawberries 806 and deli meat 808. Purifier light 802 can determine objectives related to refrigerator 804. In one example, purifier light 802 can pre-configured with objectives from a manufacturer of refrigerator 804. In another example, purifier light 802 can employ artificial intelligence to determine objectives related to refrigerator 804.

In an example, purifier light 802 can determine an objective of maintaining freshness of contents of the refrigerator 804. Purifier light 802 can employ instruments 510 for detecting refrigerator 804 contents, such as strawberries 806 and deli meat 808. Furthermore, purifier light 802 can employ instruments 510 to detect a contaminant in refrigerator 804 that can impact freshness of strawberries 806 and/or deli meat 808 and the level of contamination. If purifier light 702d determines that the contaminant satisfy the defined cleanliness criterion, purifier light 702d can perform an action, such as projecting a particular light output or employing an instrument 510, to reduce the contaminant to satisfy the defined cleanliness criterion. In another example, can perform an action, such as projecting a particular light output or employing an instrument 510, that slows down the decomposition of the strawberries 806 and/or deli meat 808.

FIGS. 9A-9D illustrates a block diagram of an example, non-limiting bed 902 in which purifier light 906 is installed in headboard 904 in accordance with one or more embodiments described herein. Purifier light 906 can be or include portions of purifier light 502. For example, purifier light 906 can be purifier light bulb 102 installed as a retrofit into a light fixture 114 in headboard 904. In another example, purifier light 906 can be purifier light 200 where purifier light fixture 202 replaces a light fixture 114 in headboard 904 and has purifier light bulb 102 installed. Purifier light 906 can determine objectives related to bed 902. In one example, purifier light 906 can be pre-configured with objectives from a manufacturer of bed 902. In another example, purifier light 906 can employ artificial intelligence to determine objectives related to bed 902. In an example, purifier light 906 can determine an object to have a contaminant of bed 902 satisfy a defined cleanliness criterion.

Figure 9A:
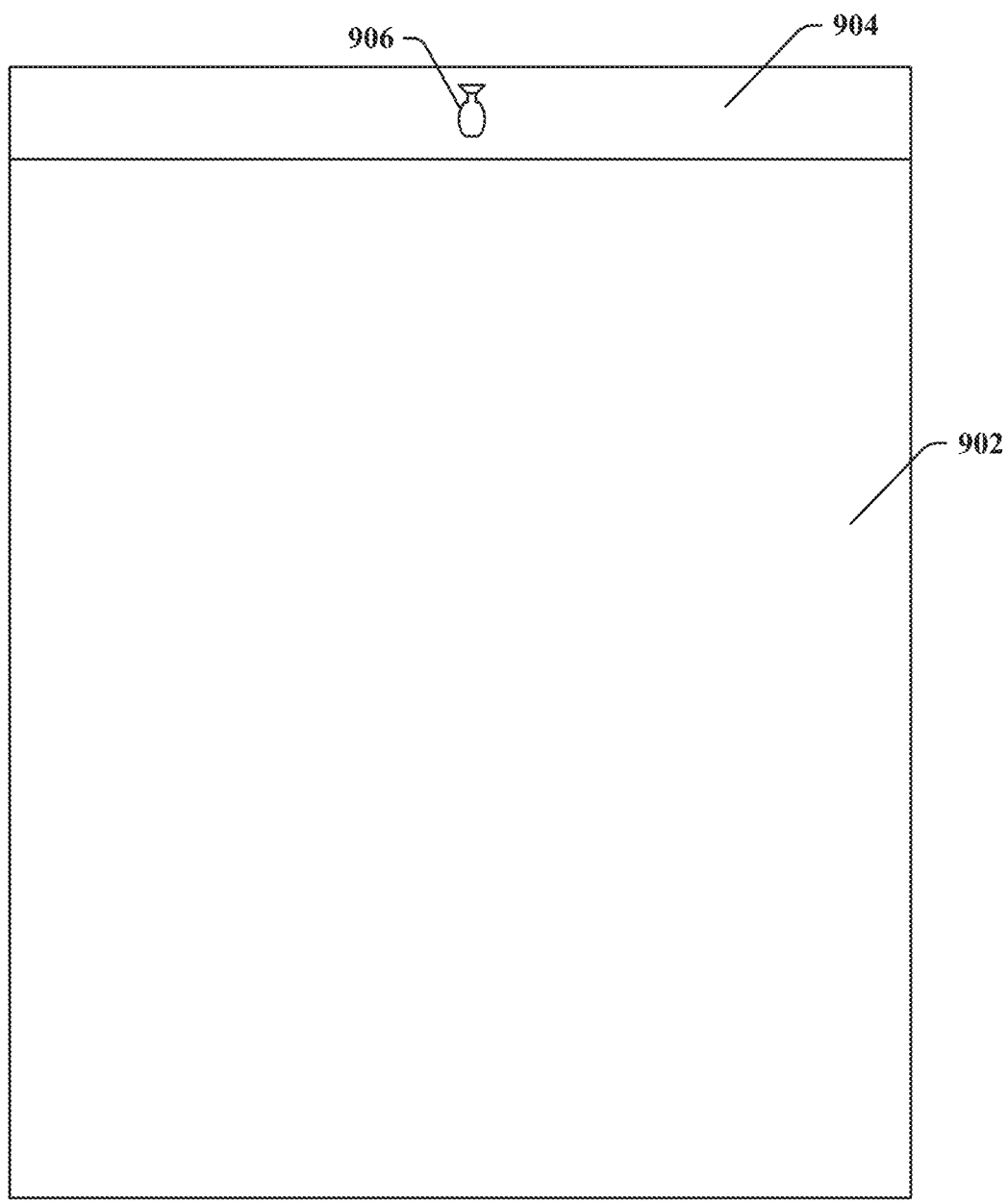
FIGS. 9A-9D illustrates a block diagram of an example, non-limiting environment in which a purifier light is installed in accordance with one or more embodiments described herein.
Figure 9B:
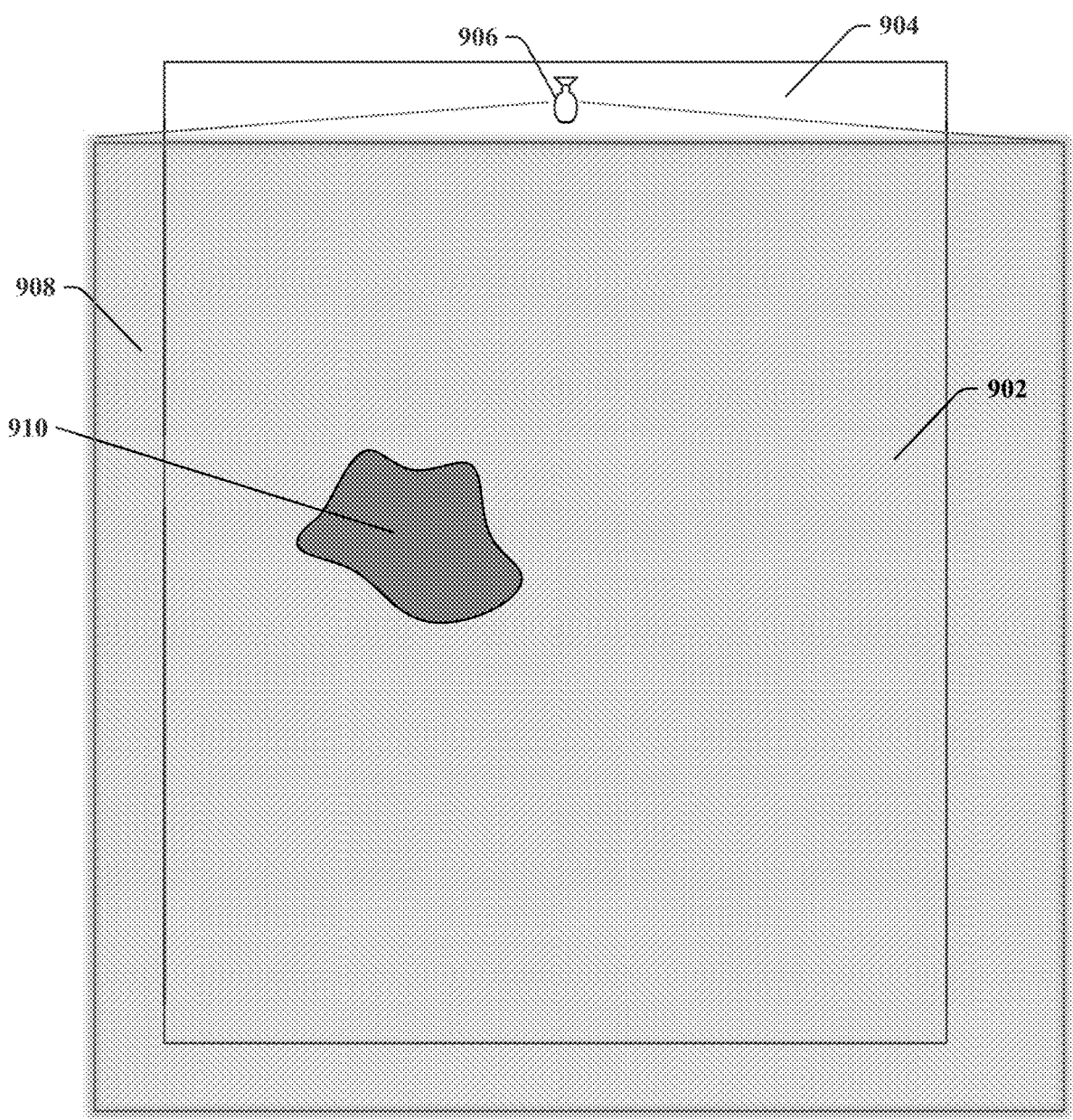

Referring to FIG. 9B, purifier light 906 can project a light output 908 with defined electromagnetic characteristics that enables an instrument 510 of purifier light 906 to detect contaminant 910 on bed 902. Purifier light 906 can determine if a level of contamination of contaminant 910 on bed 902 does not satisfy the defined cleanliness criteria. If the level of contamination of contaminant 910 on bed 902 does not satisfy the defined cleanliness criteria, purifier light 906 can perform an action to reduce the level of contamination of contaminant 910 on bed 902 to satisfy the defined cleanliness criteria.

Figure 9C:
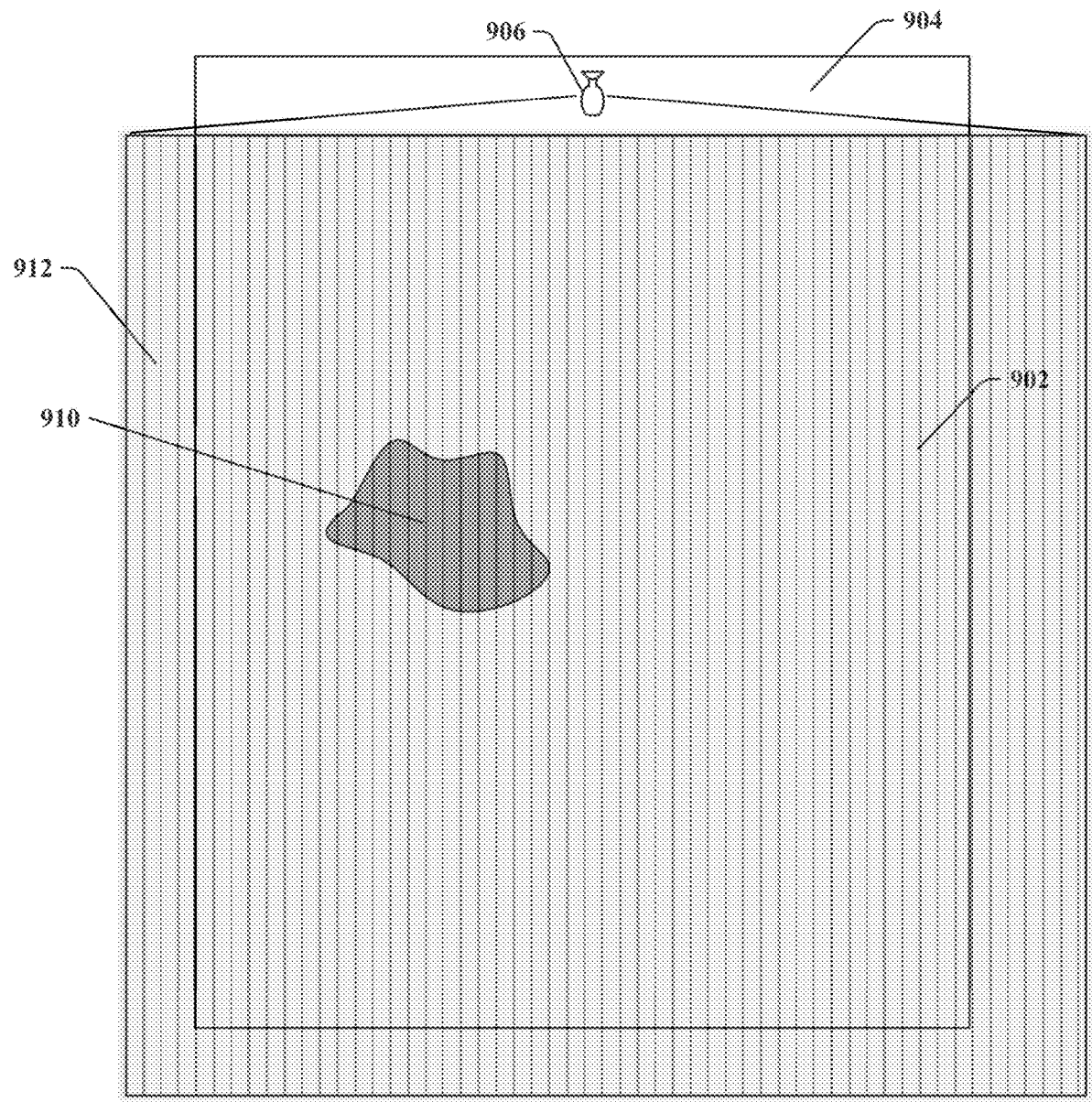

Referring to FIG. 9C, in response to the level of contamination of contaminant 910 on bed 902 not satisfying the defined cleanliness criteria, purifier light 906 can project a light output 912 with defined electromagnetic characteristics that reduce contaminant 910 until the level of contamination of contaminant 910 on bed 902 satisfies the defined cleanliness criteria.

Figure 9D:
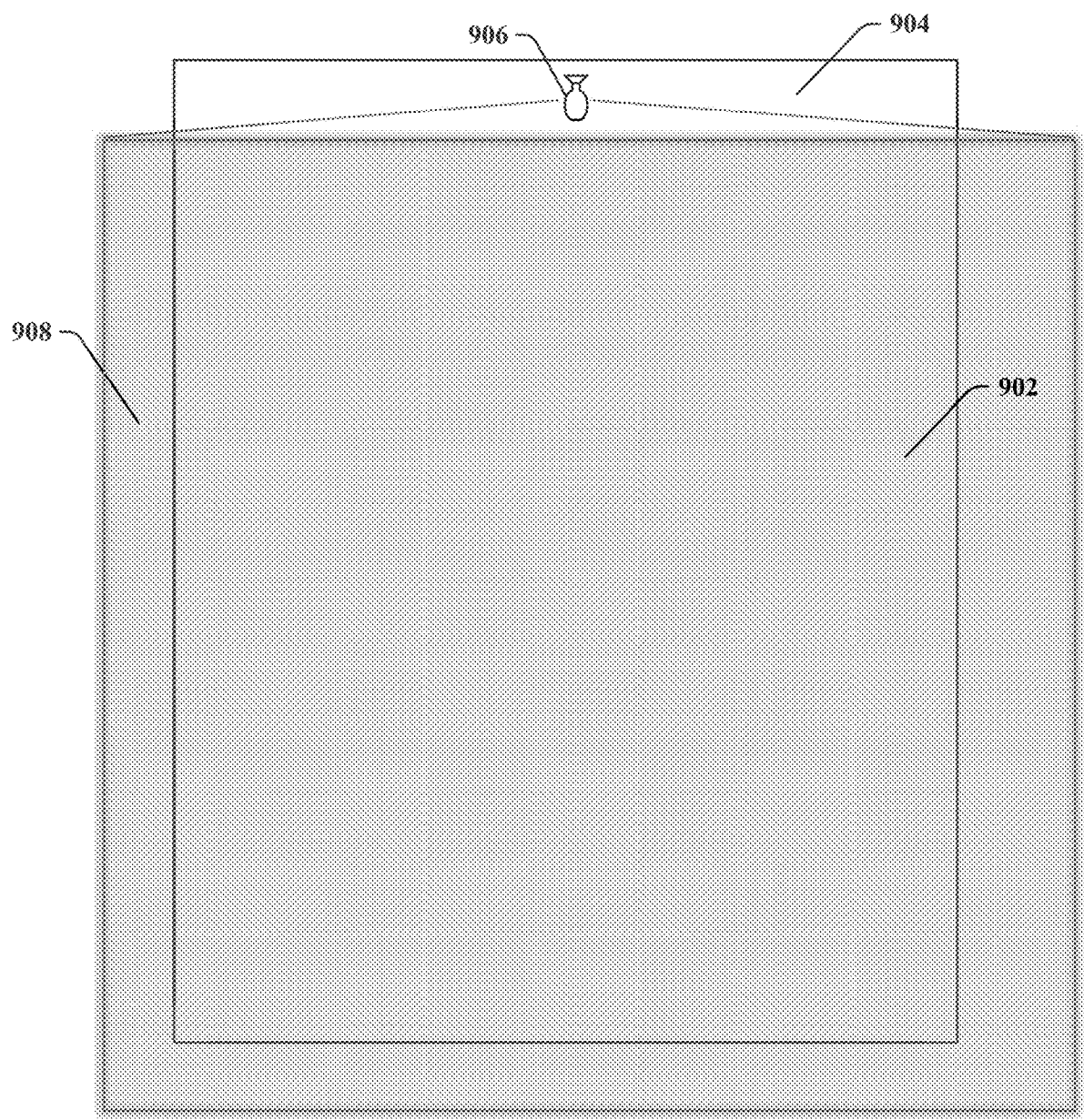

Referring to FIG. 9D, purifier light 906 can again project light output 908 that enables an instrument 510 of purifier light 906 to detect contaminant 910 on bed 902 and confirm that the level of contamination of contaminant 910 on bed 902 satisfies the defined cleanliness criteria.

In another example, the purifier light 906 can detect pests (e.g. bed bugs, fleas, ticks, etc.) and adjust lighting output and/or use other instruments (e.g. audio, scent, blower, chemical sprayer, etc.) to kill or drive away the pests on bed 902.

Figure 10:
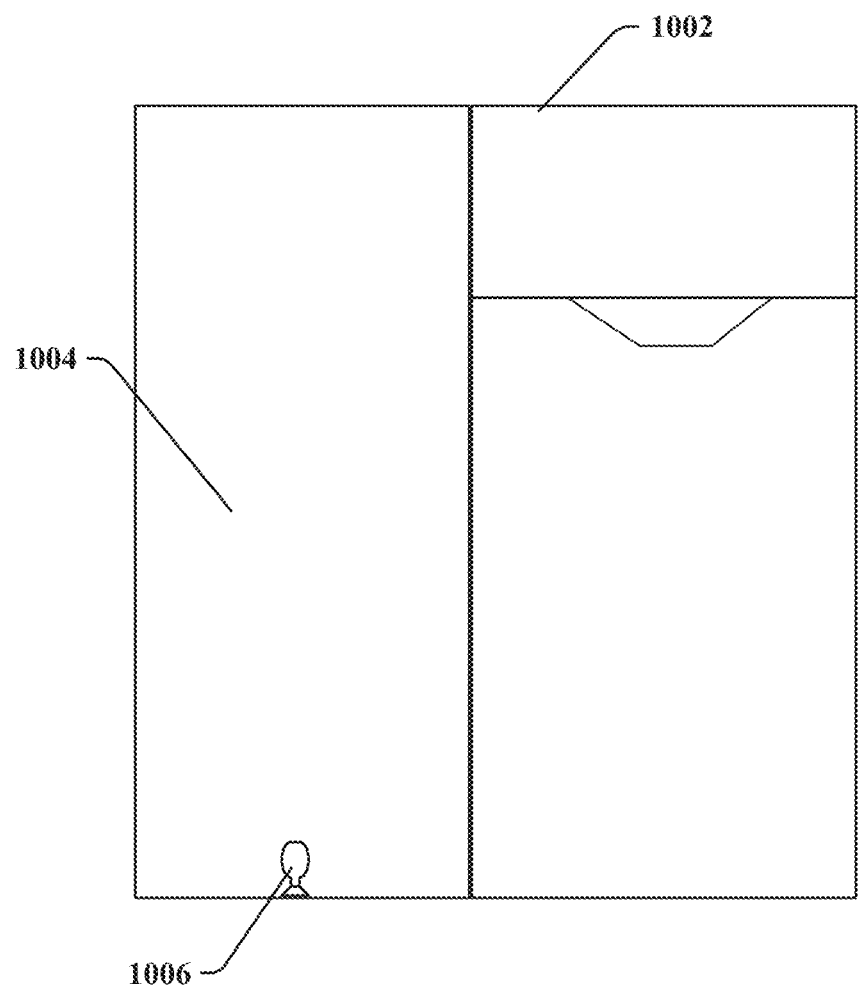
FIG. 10 illustrates a block diagram of an example, non-limiting environment in which a purifier light is installed in accordance with one or more embodiments described herein.

FIG. 10 illustrates a block diagram of an example, non-limiting coffee maker 1002 in which purifier light 1006 is installed in water tank 1004 in accordance with one or more embodiments described herein. Purifier light 1006 can be or include portions of purifier light 502. For example, purifier light 1006 can be purifier light bulb 102 installed as a retrofit into a light fixture 114 in water tank 1004. In another example, purifier light 1006 can be purifier light 200 where purifier light fixture 202 replaces a light fixture 114 in water tank 1004 and has purifier light bulb 102 installed. Purifier light 1006 can determine objectives related to coffee maker 1002. In one example, purifier light 1006 can be pre-configured with objectives from a manufacturer of coffee maker 1002. In another example, purifier light 1006 can employ artificial intelligence to determine objectives related to coffee maker 1002. In an example, purifier light 1006 can determine an object to have one or more contaminants of water tank 1004 satisfy a defined cleanliness criterion.

Purifier light 1006 can project a light output with defined electromagnetic characteristics and/or employ an instrument 510 of purifier light 1006 to detect the one or more contaminants of water tank 1004. Purifier light 1006 can determine if a level of contamination of a contaminant of water tank 1004 does not satisfy the defined cleanliness criteria. If the level of contamination of the contaminant 910 of water tank 1004 does not satisfy the defined cleanliness criteria, purifier light 1006 can perform an action to reduce the level of contamination of the contaminant of water tank 1004 to satisfy the defined cleanliness criteria.

Referring back to FIG. 5, purifier light 502 can implement a variety of functionality in various embodiments. For example, purifier light 502 can determine its own operational state (e.g. fault, nearing end of life, etc.) and re-order a replacement or schedule service based on its operational state. In another example, a faucet (not shown) can have a purifier light 502 installed in the water spout that detect and cleans water of contaminants as the water passes through the spout to satisfy a defined cleanliness criterion. Furthermore, the spout can be a clear unbreakable material (e.g. glass, polymer, metal) and the purifier light can change colors as a decorative feature, as well as provide a warning color to indicate the presence of a contaminant in the spout and/or water.

In further example, purifier light 502 can detect contaminants in the air, adjust its light output, employ tools, or instruct other devices/systems on operations to reduce the contaminant to satisfy a defined cleanliness criterion. For example, the purifier light can employ an instrument (e.g. scent sprayer, air blower, etc.) to address the contaminant. In another example, purifier light can instruct an HVAC system to adjust air filtering to neutralize the contaminant. In a further example, the purifier light can provide an alert (e.g. text, audio, visual, etc.) to a person of the existence of the contaminant.

In another example, the purifier light 502 can be installed in a pool (e.g. swimming, wading, fish pond, etc.) and detect conditions of the pool (e.g. contaminants, chemical state, occupants (e.g. fish, swimmers), etc.) and project a light output with defined electromagnetic characteristics to reduce contaminants. Furthermore, purifier light 502 can instruct an automated pool filter/cleaning system in operations to optimize conditions of the pool for the occupants as determined by purifier light 502. For example, purifier light 502 can determine that swimmers have irritated eyes and instruct an automated chemical dispenser to decrease pool chemicals. In another example, purifier light 502 can determine that no occupants are in the pool, and instruct the automated chemical dispenser to deliver pool chemicals, such as in quantities determined by purifier light 502 for current pool conditions. Alternatively, purifier light 502 can send an alert to a pool cleaning service when the pool needs to be serviced. In an additional example, purifier light 502 can determine health condition of fish in a pond and project a light output with defined electromagnetic characteristics and/or instruments 510 to maintain and/or improve the health condition of the fish, such to eliminate disease, increase size, improve mobility, or any other suitable health condition of a fish.

In an additional example, the purifier light 502 can be installed in a medical environment (e.g. a medical examination room, a surgical room, a laboratory, an intravenous infusion room, a physical therapy room, a hospital room, a medical waiting room, or any other suitable medical facility). Purifier light 502 can automatically perform actions to maintain contaminants in the medical environment to satisfy a defined cleanliness criterion. For example, purifier light 502 can perform cleaning actions between use of the medical environment. In an example, purifier light 502 can perform a light cleaning action in the limited time between patients occupying a room for a medical examination and/or procedure. In another example, purifier light 502 can perform a deep cleaning action in the extended time between the last use of a room at the end of a work day and the use of the room at the beginning of the next work day. In a further example, purifier light 502 can detect when a room is unoccupied and perform actions to maintain contaminants in the medical environment to satisfy a defined cleanliness criterion. In an additional example, purifier light 502 can detect when a medical room has a contamination level of a contaminant that does not satisfy a defined cleanliness criterion and provide a notification to a device associated with a medical staff member to avoid use of the medical room until purifier light 502 and/or other means (e.g. cleaning staff, etc.) can reduce the contamination level of the contaminant to satisfy the defined cleanliness criterion. Purifier light 502 can provide another notification to the device associated with the medical staff member when the contamination level of the contaminant satisfies the defined cleanliness criterion. In an additional example, purifier light 502 can be installed in a medical waiting room, and detect a patient with a transmittable pathogen, and a notification to a device associated with a medical staff member to recommend isolation of the patient from other patients. In addition, purifier light 502 can perform an action to reduce the transmittable pathogen and/or keep the transmittable pathogen away from other patents, such as through projection of light output with defined electromagnetic characteristics to kill the transmittable pathogen, and/or controlling airflow in the medical waiting room.

In a further example, purifier light 502 can have a nanocoating that facilitates keeping purifier light 502 clean to mitigate the need for manual cleaning.

While FIGS. 5 and 6 depict separate components in purifier light 502, it is to be appreciated that two or more components can be implemented in a common component. Further, it is to be appreciated that the design of the purifier light 502 can include other component selections, component placements, etc., to facilitate determining characteristics of the environment in which the purifier light 502 is installed, determining capabilities of purifier light 502, determining one or more objectives of the installation of purifier light 502, performing a self-configuration of purifier light 502 according to the determined one or more objectives, and determining and executing suitable actions for purifier light 502 to perform to achieve the determined one or more objectives in accordance with one or more embodiments described herein. Moreover, the aforementioned systems and/or devices have been described with respect to interaction between several components. It should be appreciated that such systems and components can include those components or sub-components specified therein, some of the specified components or sub-components, and/or additional components. Sub-components could also be implemented as components communicatively coupled to other components rather than included within parent components. Further yet, one or more components and/or sub-components can be combined into a single component providing aggregate functionality. The components can also interact with one or more other components not specifically described herein for the sake of brevity, but known by those of skill in the art.

Further, some of the processes performed may be performed by specialized computers for carrying out defined tasks related to determining characteristics of the environment in which the purifier light 502 is installed, determining capabilities of purifier light 502, determining one or more objectives of the installation of purifier light 502, performing a self-configuration of purifier light 502 according to the determined one or more objectives, and determining and executing suitable actions for purifier light 502 to perform to achieve the determined one or more objectives. The subject computer processing systems, methods apparatuses and/or computer program products can be employed to solve new problems that arise through advancements in technology, computer networks, the Internet and the like. The subject computer processing systems, methods apparatuses and/or computer program products can provide technical improvements to systems for determining characteristics of the environment in which the purifier light 502 is installed, determining capabilities of purifier light 502, determining one or more objectives of the installation of purifier light 502, performing a self-configuration of purifier light 502 according to the determined one or more objectives, and determining and executing suitable actions for purifier light 502 to perform to achieve the determined one or more objectives by improving processing efficiency among processing components in these systems, reducing delay in processing performed by the processing components, reducing memory requirements, and/or improving the accuracy in which the processing systems are determining characteristics of the environment in which the purifier light 502 is installed, determining capabilities of purifier light 502, determining one or more objectives of the installation of purifier light 502, performing a self-configuration of purifier light 502 according to the determined one or more objectives, and determining and executing suitable actions for purifier light 502 to perform to achieve the determined one or more objectives.

It is to be appreciated that the any criteria or thresholds disclosed herein can be pre-defined, operator specified, and/or dynamically determined, for example, based on learning algorithms.

The embodiments of devices described herein can employ artificial intelligence (AI) to facilitate automating one or more features described herein. The components can employ various AI-based schemes for carrying out various embodiments/examples disclosed herein. In order to provide for or aid in the numerous determinations (e.g., determine, ascertain, infer, calculate, predict, prognose, estimate, derive, forecast, detect, compute) described herein, components described herein can examine the entirety or a subset of the data to which it is granted access and can provide for reasoning about or determine states of the system, environment, etc. from a set of observations as captured via events and/or data. Determinations can be employed to identify a specific context or action, or can generate a probability distribution over states, for example. The determinations can be probabilistic—that is, the computation of a probability distribution over states of interest based on a consideration of data and events. Determinations can also refer to techniques employed for composing higher-level events from a set of events and/or data.

Such determinations can result in the construction of new events or actions from a set of observed events and/or stored event data, whether or not the events are correlated in close temporal proximity, and whether the events and data come from one or several event and data sources. Components disclosed herein can employ various classification (explicitly trained (e.g., via training data) as well as implicitly trained (e.g., via observing behavior, preferences, historical information, receiving extrinsic information, etc.)) schemes and/or systems (e.g., support vector machines, neural networks, expert systems, Bayesian belief networks, fuzzy logic, data fusion engines, etc.) in connection with performing automatic and/or determined action in connection with the claimed subject matter. Thus, classification schemes and/or systems can be used to automatically learn and perform a number of functions, actions, and/or determination.

A classifier can map an input attribute vector, z=(z1, z2, z3, z4, zn), to a confidence that the input belongs to a class, as by f(z)=confidence(class). Such classification can employ a probabilistic and/or statistical-based analysis (e.g., factoring into the analysis utilities and costs) to determinate an action to be automatically performed. A support vector machine (SVM) is an example of a classifier that can be employed. The SVM operates by finding a hyper-surface in the space of possible inputs, where the hyper-surface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and/or probabilistic classification models providing different patterns of independence can be employed. Classification as used herein also is inclusive of statistical regression that is utilized to develop models of priority.

Figure 11:
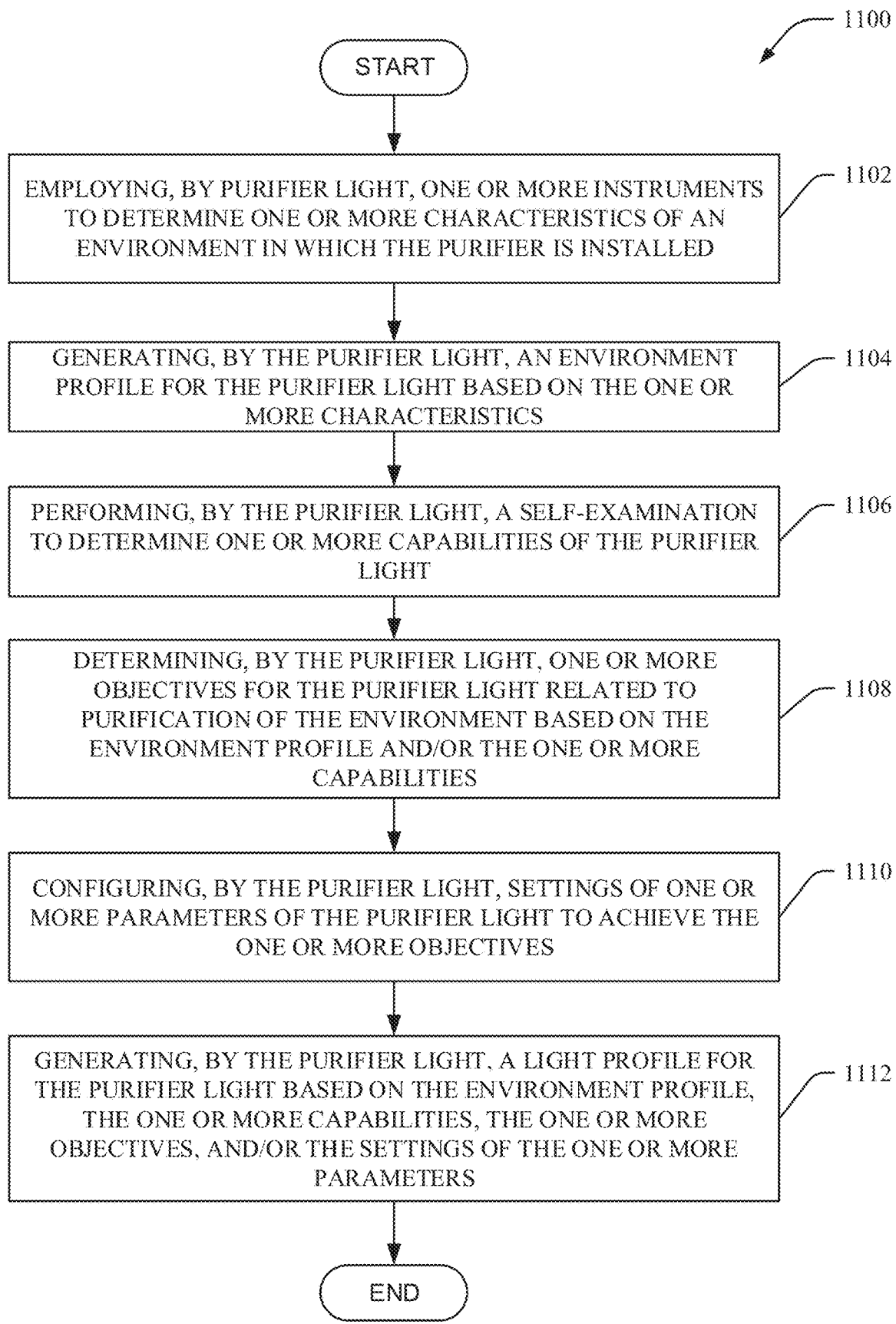
FIG. 11 illustrates a flow diagram of an example, non-limiting computer-implemented method that facilitates self-configuration of a purifier light in accordance with one or more embodiments described herein.

FIG. 11 illustrates a flow diagram of an example, non-limiting computer-implemented method 1100 that facilitates purifier light 502 determining characteristics of the environment in which the purifier light 502 is installed, determining capabilities of purifier light 502, determining one or more objectives of the installation of purifier light 502, and performing a self-configuration of purifier light 502 according to the determined one or more objectives in accordance with one or more embodiments described herein. Repetitive description of like elements employed in other embodiments described herein is omitted for sake of brevity.

At 1102, method 1100 comprises employing, by purifier light, one or more instruments to determine one or more characteristics of an environment in which the purifier is installed (e.g., via configuration component 602, purification component 504, and/or purifier light 502). At 1104, method 1100 comprises generating, by the purifier light, an environment profile for the purifier light based on the one or more characteristics (e.g., via configuration component 602, purification component 504, and/or purifier light 502). At 1106, method 1100 comprises performing, by the purifier light, a self-examination to determine one or more capabilities of the purifier light (e.g., via configuration component 602, purification component 504, and/or purifier light 502). At 1108, method 1100 comprises determining, by the purifier light, one or more objectives for the purifier light related to purification of the environment based on the environment profile and/or the one or more capabilities (e.g., via configuration component 602, purification component 504, and/or purifier light 502). At 1110, method 1100 comprises configuring, by the purifier light, settings of one or more parameters of the purifier light to achieve the one or more objectives (e.g., via configuration component 602, purification component 504, and/or purifier light 502). At 1112, method 1100 comprises generating, by the purifier light, a light profile for the purifier light based on the environment profile, the one or more capabilities, the one or more objectives, and/or the settings of the one or more parameters (e.g., via configuration component 602, purification component 504, and/or purifier light 502).

Figure 12:
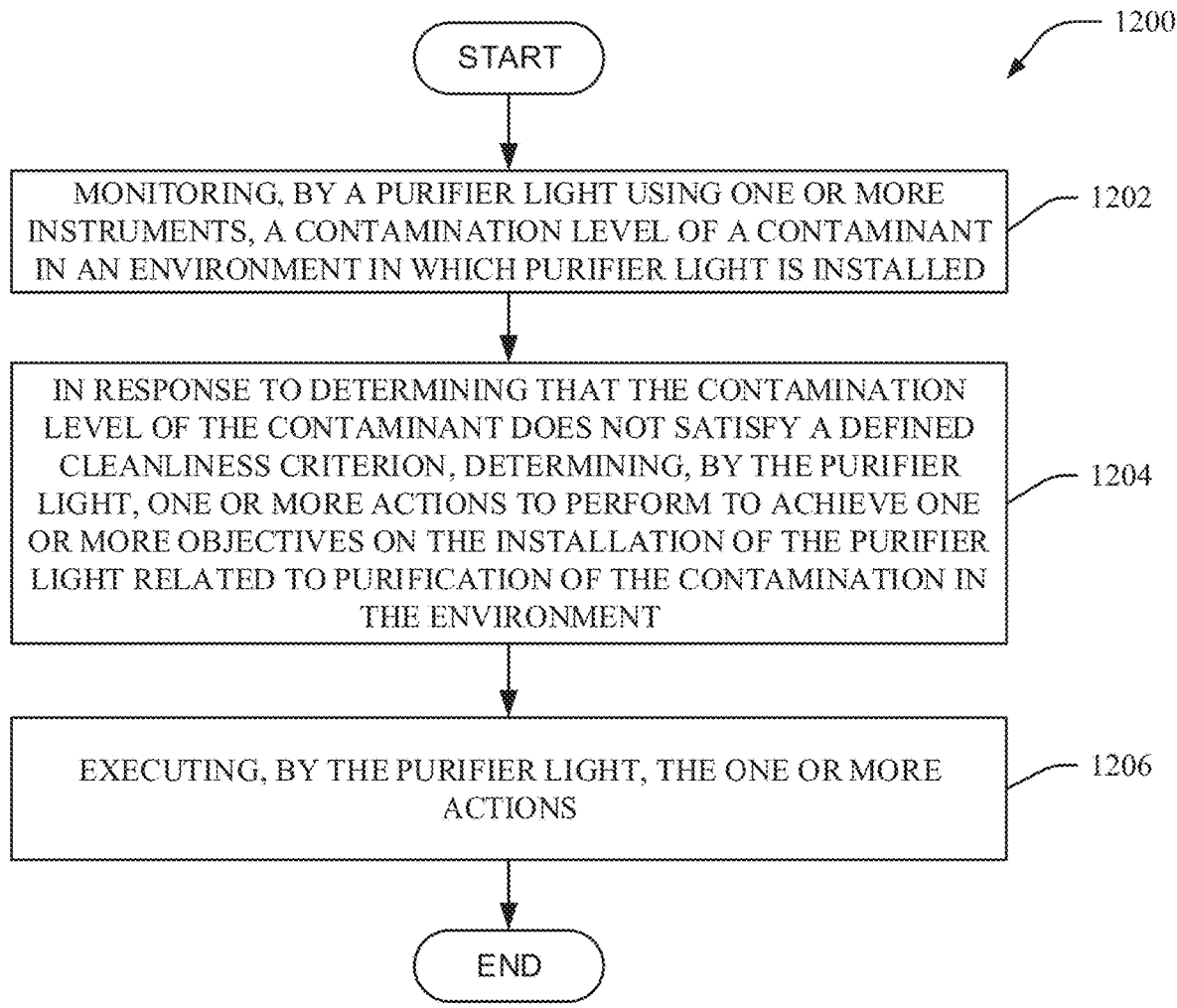
FIG. 12 illustrates a flow diagram of an example, non-limiting computer-implemented method that facilitates operation of a purifier light in accordance with one or more embodiments described herein.

FIG. 12 illustrates a flow diagram of an example, non-limiting computer-implemented method 1200 that facilitates purifier light 502 determining and executing suitable actions for purifier light 502 to perform to achieve the determined one or more objectives in accordance with one or more embodiments described herein. Repetitive description of like elements employed in other embodiments described herein is omitted for sake of brevity.

At 1202, method 1200 comprises monitoring, by a purifier light using one or more instruments, a contamination level of a contaminant in an environment in which purifier light is installed (e.g., via operation component 604, purification component 504, and/or purifier light 502). At 1204, method 1200 comprises in response to determining that the contamination level of the contaminant does not satisfy a defined cleanliness criterion, determining, by the purifier light, one or more actions to perform to achieve one or more objectives on the installation of the purifier light related to purification of the environment (e.g., via operation component 604, purification component 504, and/or purifier light 502). At 1206, method 1200 comprises executing, by the purifier light, the one or more actions (e.g., via operation component 604, purification component 504, and/or purifier light 502).

For simplicity of explanation, the computer-implemented methodologies are depicted and described as a series of acts. It is to be understood and appreciated that the subject innovation is not limited by the acts illustrated and/or by the order of acts, for example acts can occur in various orders and/or concurrently, and with other acts not presented and described herein. Furthermore, not all illustrated acts can be required to implement the computer-implemented methodologies in accordance with the disclosed subject matter. In addition, those skilled in the art will understand and appreciate that the computer-implemented methodologies could alternatively be represented as a series of interrelated states via a state diagram or events. Additionally, it should be further appreciated that the computer-implemented methodologies disclosed hereinafter and throughout this specification are capable of being stored on an article of manufacture to facilitate transporting and transferring such computer-implemented methodologies to computers. The term article of manufacture, as used herein, is intended to encompass a computer program accessible from any computer-readable device or storage media.

Figure 13:
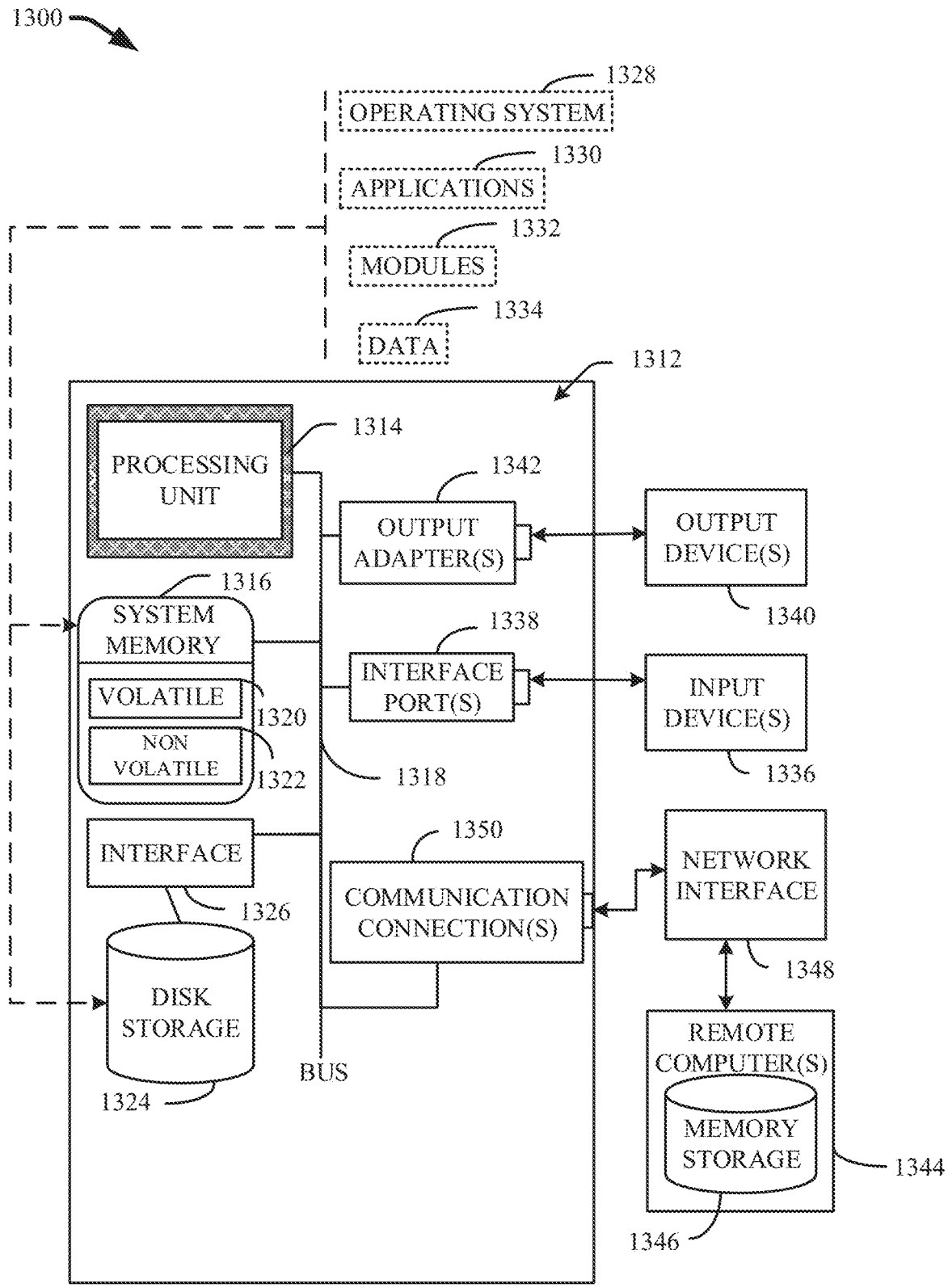
FIG. 13 illustrates a block diagram of an example, non-limiting operating environment in which one or more embodiments described herein can be facilitated.

In order to provide a context for the various aspects of the disclosed subject matter, FIG. 13 as well as the following discussion are intended to provide a general description of a suitable environment in which the various aspects of the disclosed subject matter can be implemented. FIG. 13 illustrates a block diagram of an example, non-limiting operating environment in which one or more embodiments described herein can be facilitated. Repetitive description of like elements employed in other embodiments described herein is omitted for sake of brevity.

With reference to FIG. 13, a suitable operating environment 1300 for implementing various aspects of this disclosure can also include a computer 1312. The computer 1312 can also include a processing unit 1314, a system memory 1316, and a system bus 1318. The system bus 1318 couples system components including, but not limited to, the system memory 1316 to the processing unit 1314. The processing unit 1314 can be any of various available processors. Dual microprocessors and other multiprocessor architectures also can be employed as the processing unit 1314. The system bus 1318 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Firewire (IEEE 1494), and Small Computer Systems Interface (SCSI). The system memory 1316 can also include volatile memory 1320 and nonvolatile memory 1322. The basic input/output system (BIOS), containing the basic routines to transfer information between elements within the computer 1312, such as during start-up, is stored in nonvolatile memory 1322. By way of illustration, and not limitation, nonvolatile memory 1322 can include read only memory (ROM), programmable ROM (PROM), electrically programmable ROM (EPROM), electrically erasable programmable ROM (EEPROM), flash memory, or nonvolatile random access memory (RAM) (e.g., ferroelectric RAM (FeRAM). Volatile memory 1320 can also include random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM.

Computer 1312 can also include removable/non-removable, volatile/nonvolatile computer storage media. FIG. 13 illustrates, for example, a disk storage 1324. Disk storage 1324 can also include, but is not limited to, devices like a magnetic disk drive, floppy disk drive, tape drive, Jaz drive, Zip drive, LS-100 drive, flash memory card, or memory stick. The disk storage 1324 also can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage 1324 to the system bus 1318, a removable or non-removable interface is typically used, such as interface 1326. FIG. 13 also depicts software that acts as an intermediary between users and the basic computer resources described in the suitable operating environment 1300. Such software can also include, for example, an operating system 1328. Operating system 1328, which can be stored on disk storage 1324, acts to control and allocate resources of the computer 1312. System applications 1330 take advantage of the management of resources by operating system 1328 through program modules 1332 and program data 1334, e.g., stored either in system memory 1316 or on disk storage 1324. It is to be appreciated that this disclosure can be implemented with various operating systems or combinations of operating systems. A user enters commands or information into the computer 1312 through input device(s) 1336. Input devices 1336 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1314 through the system bus 1318 via interface port(s) 1338. Interface port(s) 1338 include, for example, a serial port, a parallel port, a game port, and a universal serial bus (USB). Output device(s) 1340 use some of the same type of ports as input device(s) 1336. Thus, for example, a USB port can be used to provide input to computer 1312, and to output information from computer 1312 to an output device 1340. Output adapter 1342 is provided to illustrate that there are some output devices 1340 like monitors, speakers, and printers, among other output devices 1340, which require special adapters. The output adapters 1342 include, by way of illustration and not limitation, video and sound cards that provide a means of connection between the output device 1340 and the system bus 1318. It should be noted that other devices and/or systems of devices provide both input and output capabilities such as remote computer(s) 1344.

Computer 1312 can operate in a networked environment using logical connections to one or more remote computers, such as remote computer(s) 1344. The remote computer(s) 1344 can be a computer, a server, a router, a network PC, a workstation, a microprocessor based appliance, a peer device or other common network node and the like, and typically can also include many or all of the elements described relative to computer 1312. For purposes of brevity, only a memory storage device 1346 is illustrated with remote computer(s) 1344. Remote computer(s) 1344 is logically connected to computer 1312 through a network interface 1348 and then physically connected via communication connection 1350. Network interface 1348 encompasses wire and/or wireless communication networks such as local-area networks (LAN), wide-area networks (WAN), cellular networks, etc. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL). Communication connection(s) 1350 refers to the hardware/software employed to connect the network interface 1348 to the system bus 1318. While communication connection 1350 is shown for illustrative clarity inside computer 1312, it can also be external to computer 1312. The hardware/software for connection to the network interface 1348 can also include, for exemplary purposes only, internal and external technologies such as, modems including regular telephone grade modems, cable modems and DSL modems, ISDN adapters, and Ethernet cards.

Embodiments of the present invention may be a system, a method, an apparatus and/or a computer program product at any possible technical detail level of integration. The computer program product can include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of various aspects of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to customize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments where tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or non-volatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A purifier light bulb configured for installation in a light fixture, the purifier light bulb comprising:
one or more instruments;
a memory that stores computer executable components; and
a processor that executes the computer executable components stored in the memory, wherein the computer executable components comprise:
an operation component that:
detects, via at least one instrument of the one or more instruments, a contamination level of a contaminant in an environment in which purifier light is installed that exceeds a threshold contamination level; and
performs an action to reduce the contamination level of the contaminant in the environment to not exceed the threshold contamination level.

2. The purifier light bulb of claim 1, wherein the action comprises projection of a light output from the purifier light bulb with defined electromagnetic characteristics that reduce the contamination level of the contaminant.

3. The purifier light bulb of claim 1, wherein the action comprises employment of at least one other instrument of the one or more instruments to reduce the contamination level of the contaminant.

4. The purifier light bulb of claim 1, wherein the action comprises employment at least one other instrument of the one or more instruments to remotely control a device to perform a purification function to reduce the contamination level of the contaminant.

5. The purifier light bulb of claim 1, wherein the action comprises transmission of a warning notification to a device associated with a person in the environment indicating the contamination level of the contaminant in an environment.

6. The purifier light bulb of claim 1, wherein the contaminant is at least one of a bacteria, a mold, a virus, or a chemical.

7. The purifier light bulb of claim 1, wherein the operation component performs the action at a time selected based on a learned pattern of living being activity in the environment.

8. A purifier light comprising:
a purifier light fixture;
a purifier light bulb configured for installation in the purifier light fixture;
one or more instruments located in at least one of the purifier light bulb or the purifier light fixture;
a memory that stores computer executable components; and
a processor that executes the computer executable components stored in the memory, wherein the computer executable components comprise:
an operation component that:
detects, via at least one instrument of the one or more instruments, a contamination level of a contaminant in an environment in which purifier light is installed that exceeds a threshold contamination level; and
performs at least one action to reduce the contamination level of the contaminant in the environment to below the threshold contamination level.

9. The purifier light of claim 8, wherein the at least one action comprises projection of a light output from the purifier light bulb with defined electromagnetic characteristics that reduce the contamination level of the contaminant.

10. The purifier light of claim 8, wherein the at least one action comprises employment of a chemical sprayer of the one or more instruments to spray a chemical to reduce the contamination level of the contaminant.

11. The purifier light of claim 8, wherein the at least one action comprises employment at least one other instrument of the one or more instruments to remotely control a robotic cleaning device to perform a cleaning function to reduce the contamination level of the contaminant.

12. The purifier light of claim 8, wherein the at least one action comprises transmission of a warning notification to a device associated with a person in the environment indicating the contamination level of the contaminant in an environment.

13. The purifier light of claim 8, wherein the contaminant is at least one of a bacteria, a mold, a virus, or a chemical.

14. The purifier light of claim 1, wherein the operation component performs the action at a time selected based on a learned pattern of human activity in the environment.

15. A method comprising:
identifying, by a purifier light bulb via one or more instruments of the purifier light bulb, a contamination level of a contaminant in an environment in which purifier light bulb is installed that exceeds a threshold contamination level; and
executing, by the purifier light bulb, an action to reduce the contamination level of the contaminant in the environment to not exceed the threshold contamination level.

16. The method of claim 15, wherein the executing the action comprises projecting a light output from the purifier light bulb with defined electromagnetic characteristics that reduce the contamination level of the contaminant.

17. The method of claim 15, wherein the executing the action comprises employing one or more other instruments of the purifier light bulb to reduce the contamination level of the contaminant.

18. The method of claim 15, wherein the executing the action comprises employing one or more other instruments of the purifier light bulb to remotely control a device to perform a purification function to reduce the contamination level of the contaminant.

19. The method of claim 15, wherein the executing the action comprises coordinating with another purifier light bulb to perform one or more additional actions in a coordinated manner to reduce the contamination level of the contaminant.

20. The method of claim 15, wherein the contaminant is at least one of a bacteria, a mold, a virus, or a chemical.

* * * * *